US008944780B2

(12) United States Patent
Reilly

(10) Patent No.: US 8,944,780 B2
(45) Date of Patent: Feb. 3, 2015

(54) PUMPING DEVICES, SYSTEMS INCLUDING MULTIPLE PISTONS AND METHODS FOR USE WITH MEDICAL FLUIDS

(75) Inventor: David M. Reilly, Pittsburgh, PA (US)

(73) Assignee: Bayer Medical Care Inc., Indianola, PA (US)

( * ) Notice: Subject to any disclaimer, the term of this patent is extended or adjusted under 35 U.S.C. 154(b) by 662 days.

(21) Appl. No.: 13/071,939

(22) Filed: Mar. 25, 2011

(65) Prior Publication Data

US 2012/0244018 A1 Sep. 27, 2012

(51) Int. Cl.

| | |
|---|---|
| ***F04B 1/12*** | (2006.01) |
| ***F04B 27/08*** | (2006.01) |
| ***F04B 1/26*** | (2006.01) |
| ***F04B 1/00*** | (2006.01) |
| ***F04B 27/00*** | (2006.01) |
| ***F04B 9/02*** | (2006.01) |
| ***F04B 9/04*** | (2006.01) |
| ***F04B 11/00*** | (2006.01) |

(52) U.S. Cl.

CPC . *F04B 1/128* (2013.01); *F04B 9/02* (2013.01); *F04B 9/042* (2013.01); *F04B 11/0058* (2013.01)

USPC ........... 417/269; 417/271; 417/454; 417/539; 137/625.48; 137/897

(58) Field of Classification Search

USPC ......... 417/254, 266, 269, 271, 415, 454, 529, 417/539; 137/625.48, 896–898

See application file for complete search history.

(56) References Cited

U.S. PATENT DOCUMENTS

| | | | | |
|---|---|---|---|---|
| 2,114,565 | A * | 4/1938 | Kovach | 417/490 |
| 3,447,479 | A | 6/1969 | Rosenberg | |
| 3,949,746 | A | 4/1976 | Wallach | |
| 3,993,061 | A | 11/1976 | O'Leary | |
| 3,994,294 | A | 11/1976 | Knute | |
| 4,032,263 | A * | 6/1977 | Pareja | 417/539 |
| 4,137,011 | A * | 1/1979 | Rock | 417/22 |

(Continued)

FOREIGN PATENT DOCUMENTS

| | | |
|---|---|---|
| DE | 43363361 | 5/1994 |
| FR | 27153101 | 7/1995 |
| GB | 1511715 | 5/1978 |

OTHER PUBLICATIONS

International Search Report for International Application No. PCT/US 98/02027 filed Feb. 5, 1998.

(Continued)

*Primary Examiner* — Peter J Bertheaud

(74) *Attorney, Agent, or Firm* — Joseph L. Kent; David Schramm; James R. Stevenson

(57) ABSTRACT

A system for delivery of medical fluid to a patient which includes a pump system and a drive system. The pump system has at least three chambers, where each chamber includes an inlet for fluid intake and an outlet for fluid expulsion, a common outlet channel in fluid communication with the outlet of each chamber, and at least three pistons, where each piston is slidably disposed within one of the chambers. The drive system includes a cam shaft having at least three cam lobes, each having a profile, and at least three cam lobe followers, each in operative connection with one of the cam lobes and adapted to be placed in operative connection with a respective piston. The profile of each of the cam lobes is adapted to provide a transient increase or spike in calculated theoretical output of the pump system to reduce periodic variation in measured output thereof.

15 Claims, 18 Drawing Sheets

(56) References Cited

U.S. PATENT DOCUMENTS

| | | | | | |
|---|---|---|---|---|---|
| 4,310,420 | A * | 1/1982 | Konishi et al. | 210/659 |
| 4,311,586 | A * | 1/1982 | Baldwin et al. | 210/101 |
| 4,475,666 | A | 10/1984 | Bilbrey et al. | |
| 4,563,175 | A | 1/1986 | LaFond | |
| 4,595,495 | A * | 6/1986 | Yotam et al. | 210/101 |
| 4,734,011 | A | 3/1988 | Hall, Jr. | |
| 4,795,441 | A | 1/1989 | Bhatt | |
| 4,838,860 | A | 6/1989 | Groshong et al. | |
| 4,846,797 | A | 7/1989 | Howson et al. | |
| 4,883,409 | A * | 11/1989 | Strohmeier et al. | 417/43 |
| 4,898,579 | A | 2/1990 | Groshong et al. | |
| 5,044,902 | A | 9/1991 | Malbec | |
| 5,066,282 | A | 11/1991 | Wijay et al. | |
| 5,078,580 | A * | 1/1992 | Miller et al. | 417/265 |
| 5,192,269 | A | 3/1993 | Poli et al. | |
| 5,197,438 | A * | 3/1993 | Kumano et al. | 123/506 |
| 5,237,309 | A | 8/1993 | Frantz et al. | |
| 5,243,982 | A | 9/1993 | Mostl et al. | |
| 5,378,231 | A | 1/1995 | Johnson et al. | |
| 5,411,485 | A | 5/1995 | Tennican et al. | |
| 5,417,667 | A | 5/1995 | Tennican et al. | |
| 5,429,485 | A | 7/1995 | Dodge | |
| 5,454,792 | A | 10/1995 | Tennican et al. | |
| 5,496,273 | A | 3/1996 | Pastrone et al. | |
| 5,529,463 | A | 6/1996 | Layer et al. | |
| 5,609,572 | A | 3/1997 | Lang | |
| 5,632,606 | A | 5/1997 | Jacobsen et al. | |
| 5,852,231 | A * | 12/1998 | Kaji | 73/61.56 |
| 5,916,197 | A | 6/1999 | Reilly | |
| 6,197,000 | B1 | 3/2001 | Reilly | |
| 8,011,897 | B2 * | 9/2011 | Raleigh et al. | 417/271 |
| 8,062,003 | B2 * | 11/2011 | Goertzen et al. | 417/269 |
| 8,133,205 | B2 * | 3/2012 | Rhinehart et al. | 604/151 |
| 2011/0152681 | A1 | 6/2011 | Reilly | |

OTHER PUBLICATIONS

Debiotech Switzerland, Sales Brochure, Lausanne 9, Switzerland, distributed week of Dec. 1, 1996 at the Radiological Society of North Americanin Chicago, Illinois.

* cited by examiner

Fig. 2C
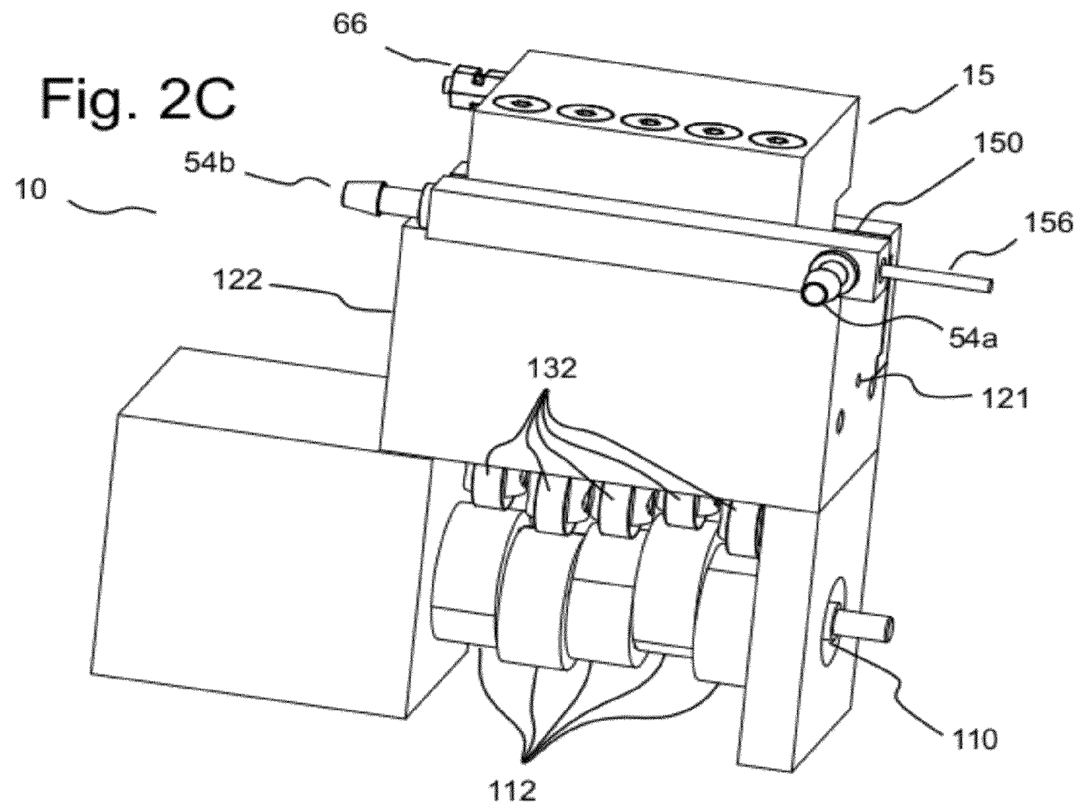
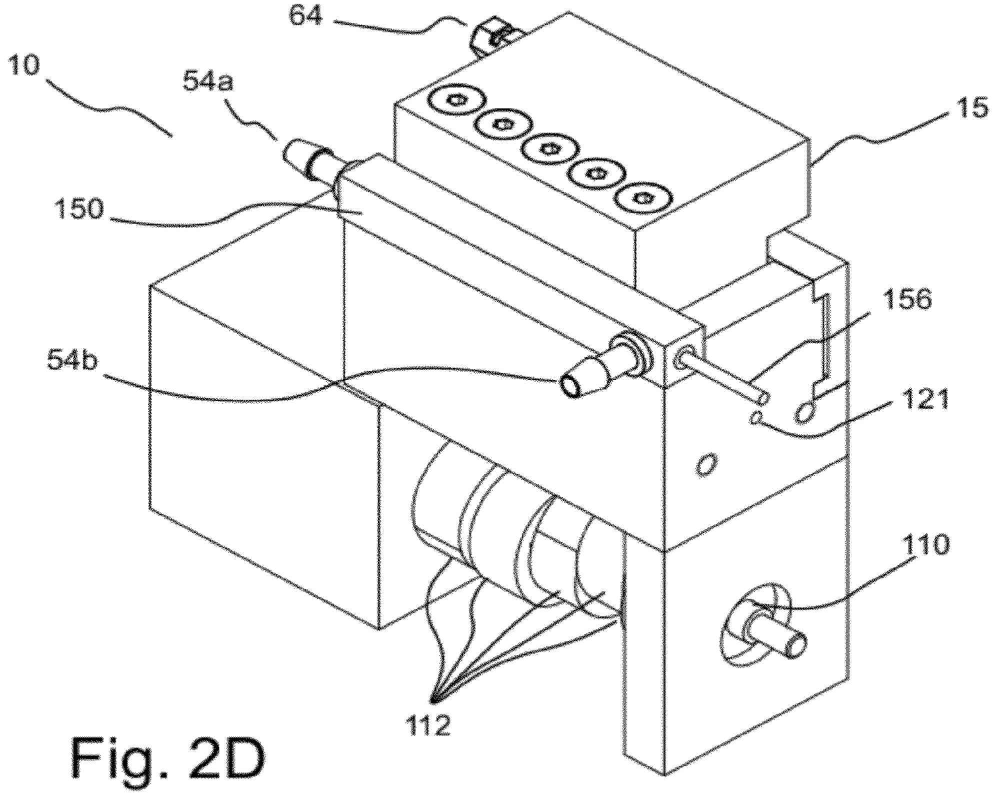
Fig. 2D

Fig. 4A
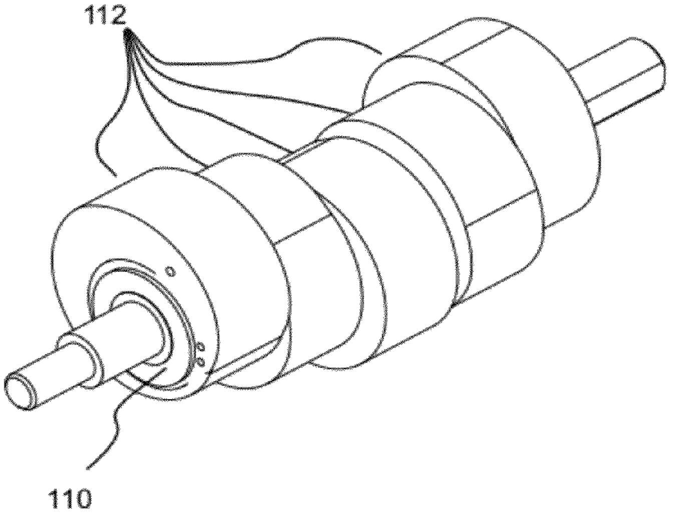
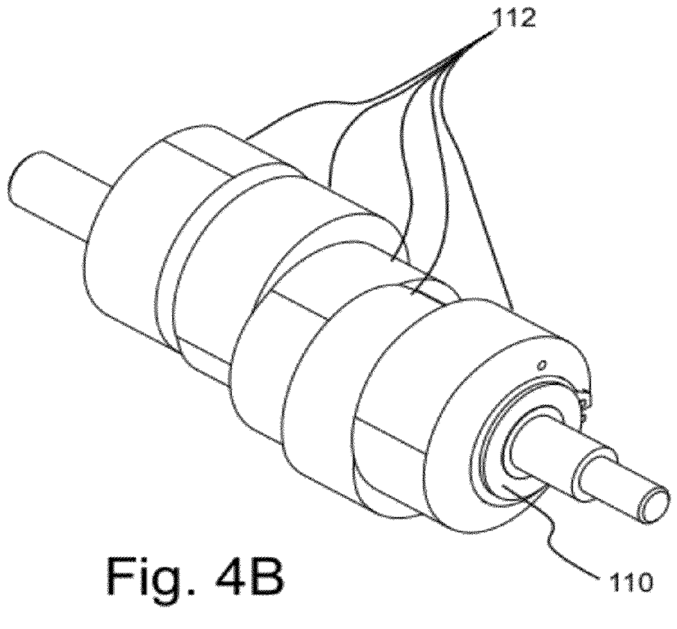
Fig. 4B
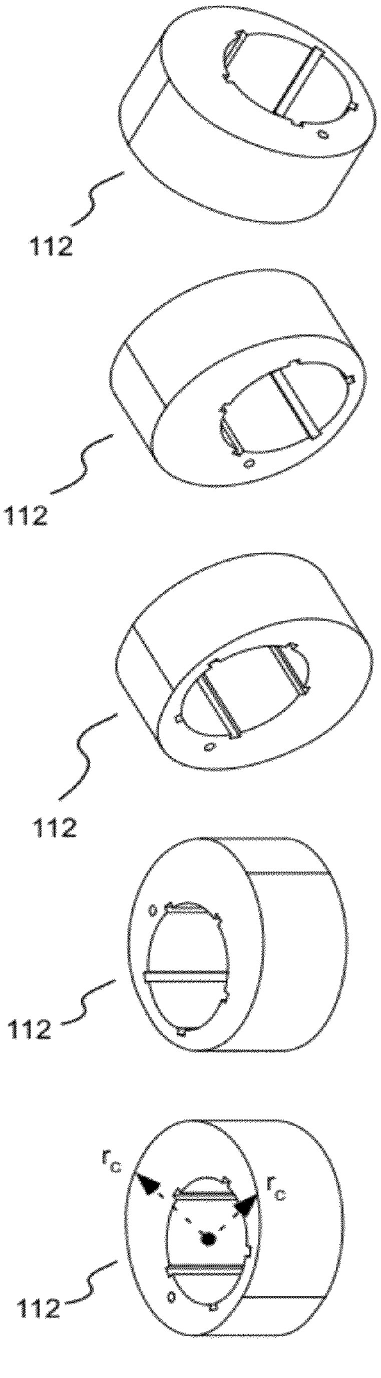
Fig. 4C

PUMPING DEVICES, SYSTEMS INCLUDING MULTIPLE PISTONS AND METHODS FOR USE WITH MEDICAL FLUIDS

RELATED APPLICATION

This application may contain subject matter that is related to that disclosed in co-pending application Ser. No. 12/974,549, filed on Dec. 21, 2010, the contents of which are incorporated herein by reference.

BACKGROUND

The following information is provided to assist the reader to understand the devices, systems and/or methods described herein and the environment in which such devices, systems and/or methods will typically be used. The terms used herein are not intended to be limited to any particular narrow interpretation unless clearly stated otherwise in this document. References set forth herein may facilitate understanding of the devices, systems and/or methods or the background. The disclosure of all references cited herein are incorporated by reference.

In many medical procedures, such as drug delivery, it is desirable to inject a fluid into a patient. Likewise, numerous types of contrast media (often referred to simply as contrast) are injected into a patient for many diagnostic and therapeutic imaging procedures. For example, contrast media are used in diagnostic procedures such as X-ray procedures (including, for example, angiography, venography and urography), CT scanning, magnetic resonance imaging (MRI), and ultrasonic imaging. Contrast media are also used during therapeutic procedures, including, for example, angioplasty and other interventional radiological procedures. Regardless of the type of procedure, any fluid injected into the patient must be sterile and contain a minimum of pyrogens.

In the case of relatively high pressure applications, such as CT and angiography, mechanized syringe injectors are often used. In general, syringe pumps can deliver a fluid with good control of both pressure and flow rate. However, flow rate acceleration of syringe injectors is limited by the inertia of the extensive drive train required to translate motor rotation into syringe plunger motion. Moreover, syringe pumps are limited in that the maximum volume that can be injected at one time is the volume of the syringe.

Various pump systems for generally continuous delivery of fluids from large volume sources of fluid are available. However, it is often difficult to accurately control the pressure and flow rate of the fluid exiting the pumping system. In relatively low pressure applications, for example, peristaltic pumps have long been used. However, peristaltic pumps are difficult to control with accuracy.

Cost-effective and efficient pumping systems including a plurality of pressurizing members actuated in a timed manner to provide pressurization for injection of contrast and other liquid media are, for example, described in U.S. Pat. Nos. 6,197,000 and 5,916,197. Although such pumps provide good control of pressure and flow rate, some variance in the pressure and/or flow rate can be experienced. Timed or sequential actuation of a plurality of pressurizing member or elements (for example, pistons, vanes, etc.) can, for example, result in pulsatile variations in pressure and/or flow rate. In general, pulsatile variations are repetitive variations or variations that occur with a certain frequency (for example, the frequency of activation of the pressurizing member(s)). U.S. patent application Ser. No. 12/974,549 discloses a number of compensating systems to reduce pulsatile flow in pump systems including a plurality of pressurizing members actuated in a timed manner.

SUMMARY

In a number of embodiments hereof, a fluid delivery system includes a pump system including a plurality of pressurizing members in which pulsatility arising from timed actuation of the pressurizing members is reduced or minimized. Such pump systems provide control of fluid pressure and flow rate over a broad range of operating pressures (for example, over operating pressures used in the injection of various contrast media and/or other medical fluids into a patient). The pump systems hereof can, for example, be used in connection with a compensating system or systems as disclosed in U.S. patent application Ser. No. 12/974,549 or can be used without such a compensating system or systems. In a number of embodiments, profiles of cam lobes of a cam shaft used to drive, for example, a plurality of pistons are adapted to reduce or eliminate pulsatility. In a number of other embodiments, independent control of each of a plurality of pressurizing members such as pistons is effected to reduce or eliminate pulsatility. In the case of independent control, feedback of data can be provided to one or more processors from one or more sensors to effect control in the manner of a servomechanism. The system can, for example, anticipate required needs and use servo feedback to fine tune or adjust the system variables or parameters to achieve a desired result of flow with little or no pulsatility.

In one aspect, a system for delivery of a medical fluid to a patient includes a pump system including a plurality of at least three chambers. Each of the plurality of chambers includes an inlet through which fluid is drawn into the chamber and an outlet from which fluid is expelled from the chamber. The pump system further includes a common outlet channel in fluid communication with the outlet of each of the plurality of chambers and a plurality of at least three pistons. Each of the pistons is slidably disposed within a respective one of the plurality of chambers. The system further includes a drive system including a cam shaft including a plurality of at least three cam lobes. Each of the plurality of cam lobes has a profile. The drive system further includes a plurality of at least three cam lobe followers. Each of the cam lobe followers is in operative connection with a respective one of the plurality of cam lobes and is adapted to be placed in operative connection with a respective one of the plurality of pistons.

The profile of each of the plurality of cam lobes is adapted to provide a transient increase or spike in calculated theoretical output of the pump system to reduce periodic variation in measured output thereof. The transient increase or spike in calculated theoretical output of the pump system can, for example, include an increase from a generally constant theoretical output, a maximum and a subsequent decrease to the generally constant theoretical output. The profile of each of the cam lobes can, for example, include a fluid delivery phase including an acceleration portion, a constant velocity portion and a deceleration portion.

In a number of embodiments, each of the plurality of pistons is in removable connection with a one of a plurality of cam lifters at a first end of the cam lifter, and one of the plurality of cam lobe followers is connected to the second end of each of the plurality of cam lifters.

In a number of embodiments, the plurality of at least three chambers includes five chambers, the plurality of at least three pistons includes five pistons, the plurality of at least three cam lobes includes five cam lobes, and the plurality of at least three cam lobe followers includes five cam lobe followers.

The system can further include a plurality of five cam lifters each having a first end and a second end. The first end of each of the cam lifters can be in removable connection with a respective one of the five pistons and the second end of each of the cam lifters is connected to a respective one of the five cam lobe followers. Each of the cam lifters can be in operative connection with a biasing element to retain the connected cam lobe follower in contact with the associated cam lobe during a chamber filling phase of the cam lobe profile. The biasing element can, for example, include a spring positioned within the cam lifter.

The system can further include five extending members, each of which passes through an extending passage defined in each of the five cam lifters to limit rotation of each of the cam lifters about a longitudinal axis thereof. Each of the cam lifters is movable relative to the extending member in the direction of the longitudinal axis of the cam lifter. Each of the biasing element/springs can abut the respective extending member at a first end thereof and an abutment member connected to the respective cam lifter at a second end thereof.

The pump system can further include a fluid intake system in fluid connection with the inlets of the plurality of chambers. In a number of embodiments, the fluid intake system includes at least two fluid inlet ports and a control system to adjust the volumetric ratio of fluid delivered from the fluid inlet ports. The fluid intake system can further include an extending channel in fluid connection with each of the fluid inlet ports. The fluid inlet ports can, for example, be spaced along the extending channel. The control member can, for example, include a sealing member in sealing engagement with the channel. The sealing member is movable within the channel to adjust the volumetric ratio. The fluid intake system can further include a plurality of spaced outlet ports in fluid connection with the extending channel and with the inlets of the plurality of chambers. The spaced outlet ports can, for example, be positioned within the channel between the positions of the fluid inlets.

In another aspect, a system for delivery of a medical fluid to a patient includes a pump system including a plurality of at least three chambers. Each of the plurality of chambers includes a piston slidably disposed therein. Each of the chambers includes an inlet through which fluid is drawn into the chamber and an outlet from which fluid is expelled from the chamber. The outlet of each of the plurality of chambers is in fluid connection with a common outlet channel. The system further includes a cam shaft including a plurality of at least three cam lobes. Each of the plurality of pistons is in operative connection with one of the plurality of cam lobes via one of a plurality of at least three cam lobe followers. The system also includes a fluid intake system in fluid connection with the inlets of the plurality of chambers. The fluid intake system includes at least two fluid inlet ports and a control system to adjust the volumetric ratio of fluid delivered from the fluid inlet ports.

As described above, the fluid inlet system can include an extending channel in fluid connection with each of the fluid inlets of the fluid inlet system. The fluid inlets can be spaced along the extending channel. The control member can, for example, include a sealing member in sealing engagement with the channel, wherein the sealing member is movable within the channel to adjust the volumetric ratio of the two fluids. The fluid inlet system can further include a plurality of spaced ports in fluid connection with the extending channel. The spaced ports are in fluid connection with the inlets of the plurality of chambers. The spaced ports can, for example, be positioned within the channel between the positions of the fluid inlets.

In a further aspect, a system for delivery of a medical fluid to a patient includes a pump system including a plurality of at least two chambers. Each of the plurality of chambers includes a piston slidably disposed therein. Each of the chambers includes an inlet through which fluid is drawn into the chamber and an outlet from which fluid is expelled from the chamber. The outlet of each of the plurality of chambers is in fluid connection with a common outlet channel. Each of the plurality of pistons is in operative connection with a one of a plurality of drive systems that is controlled independently of the others of the plurality of drive systems. In a number of embodiments, the pump system comprises at least three chambers and at least three pistons. The pump system can, for example, include at least five chambers and at least five pistons. At least one of the drive systems can, for example, included a rotary motor operatively connected to one of the plurality of pistons via a linear drive. At least one of the plurality of drive systems can, for example, include a linear motor.

In still a further aspect, a fluid mixing system includes an extending channel and at least two fluid inlet ports in fluid connection with the extending channel. The at least two fluid inlets ports are positioned at different positions along the extending channel. The fluid mixing system further includes at least one outlet port in fluid connection with the extending channel positioned between the two fluid inlet ports and a sealing member in sealing engagement with the channel, the sealing member being movable within the channel to adjust the volumetric ratio of the two fluids. The fluid mixing system can, for example, further include a plurality of spaced outlet ports in fluid connection with the extending channel. The spaced ports can be positioned within the channel between the positions of the fluid inlets.

The devices, systems and/or methods described herein, along with the attributes and attendant advantages thereof, will best be appreciated and understood in view of the following detailed description taken in conjunction with the accompanying drawings.

No. 12/974,549 and a compensating system as described in FIG. 4A of U.S. patent application Ser. No. 12/974,549, the disclosure of which is incorporated herein by reference.

Figure 2A:
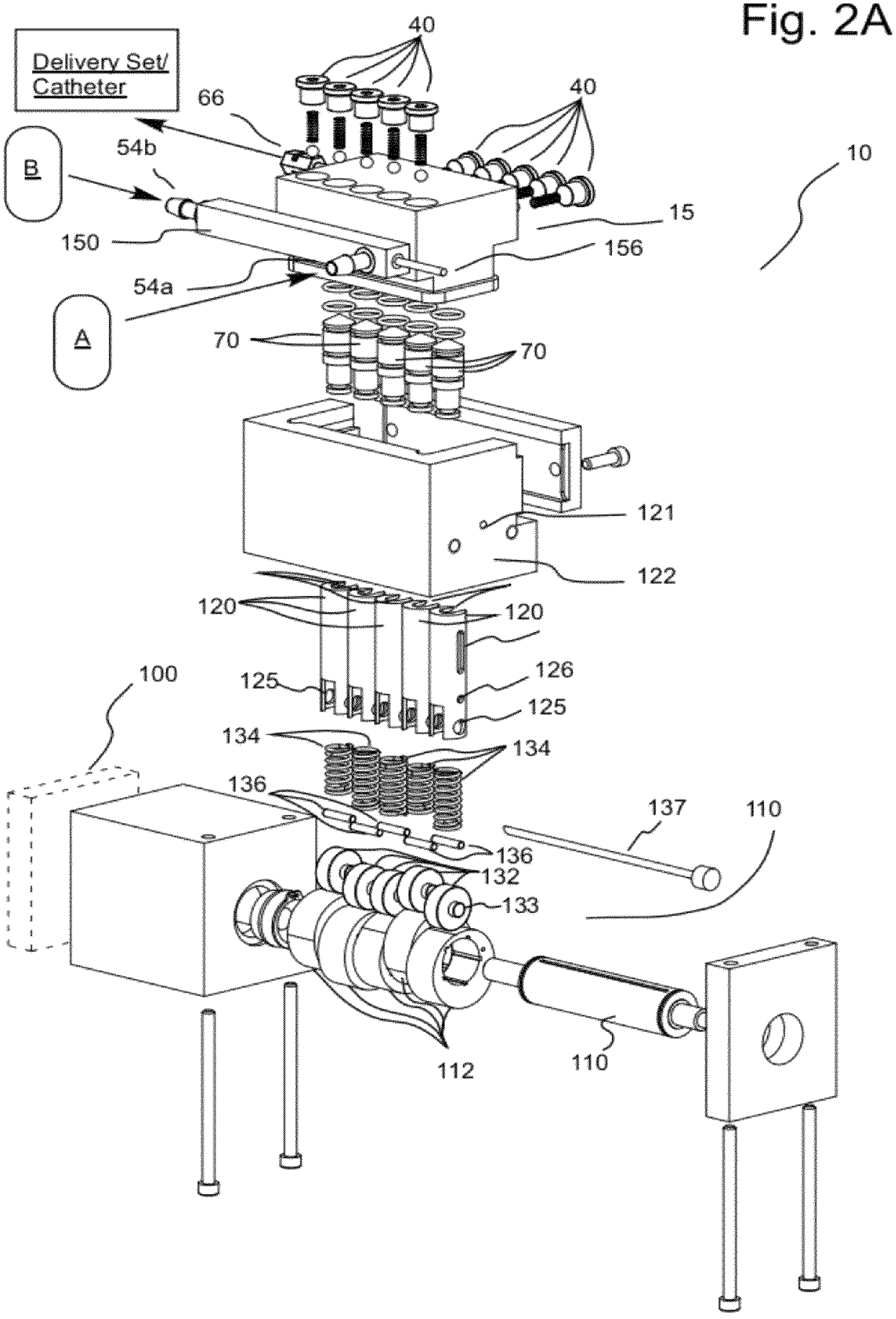

FIG. 2A illustrates a perspective, exploded view of an embodiment of a pump system.

Figure 2B:
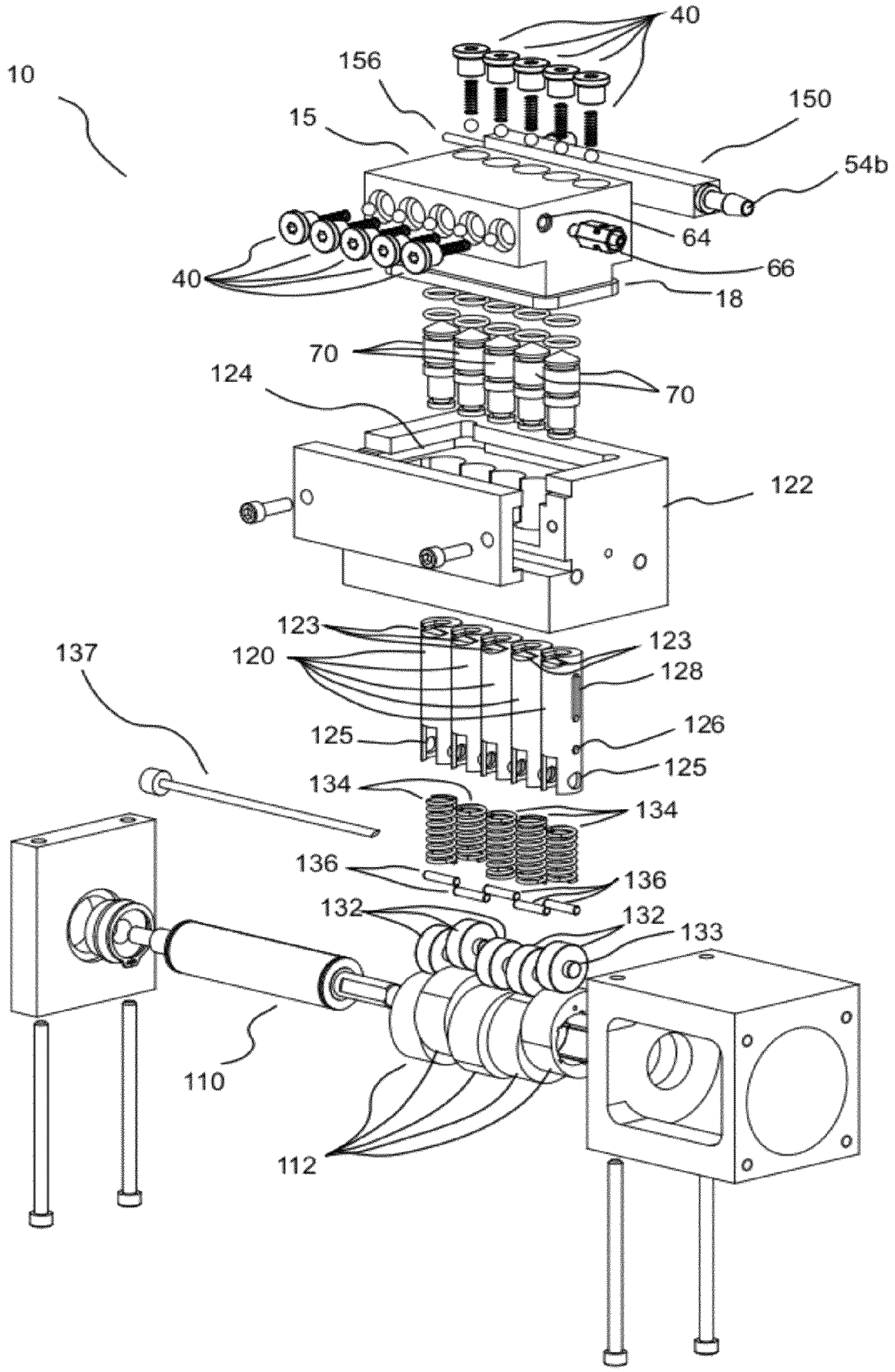

FIG. 2B illustrates another perspective, exploded view of an embodiment of a pump system.

FIG. 2C illustrates a perspective view of the pump system of FIG. 2A.

FIG. 2D illustrates another perspective view of the pump system of FIG. 2A.

Figure 2E:
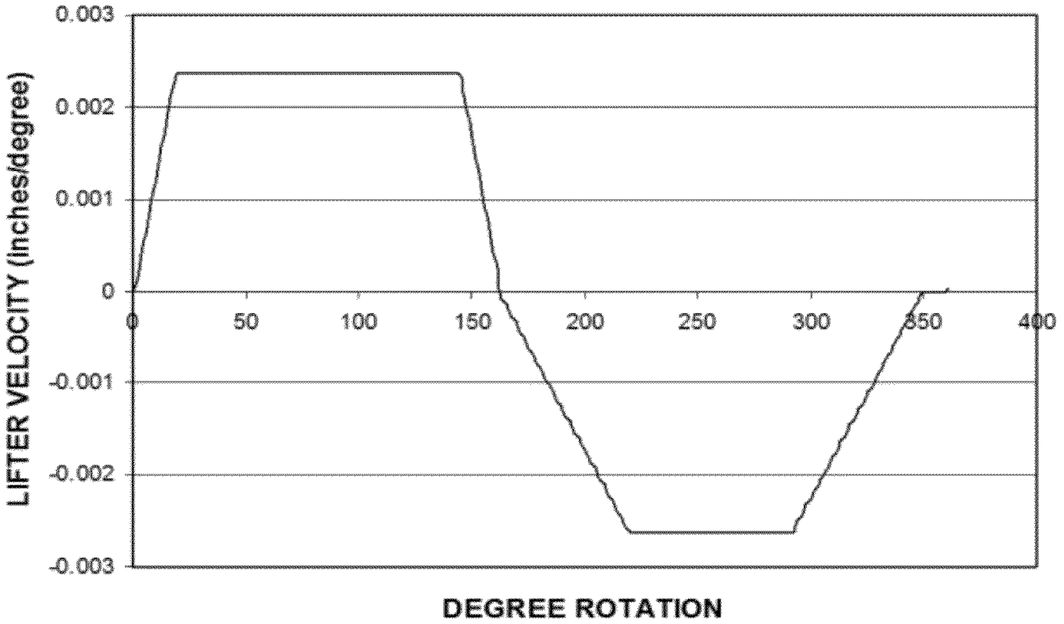

FIG. 2E illustrates cam lifter and/or piston velocity resulting from drive of a cam lifter/piston assembly via rotation of a cam lobe having a certain cam lobe profile.

Figure 2G:
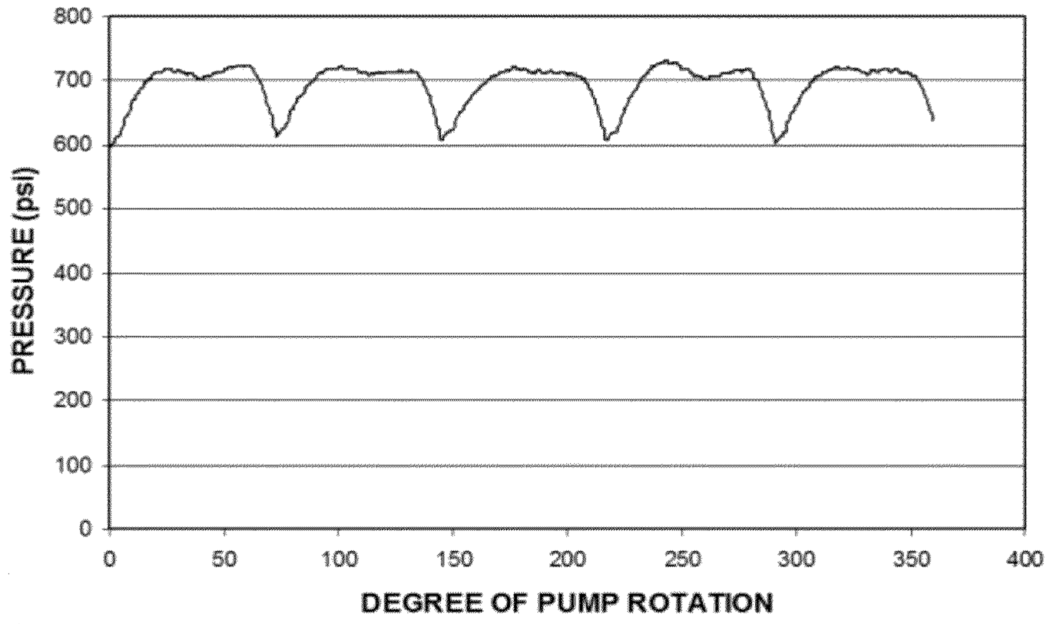
Figure 2F:
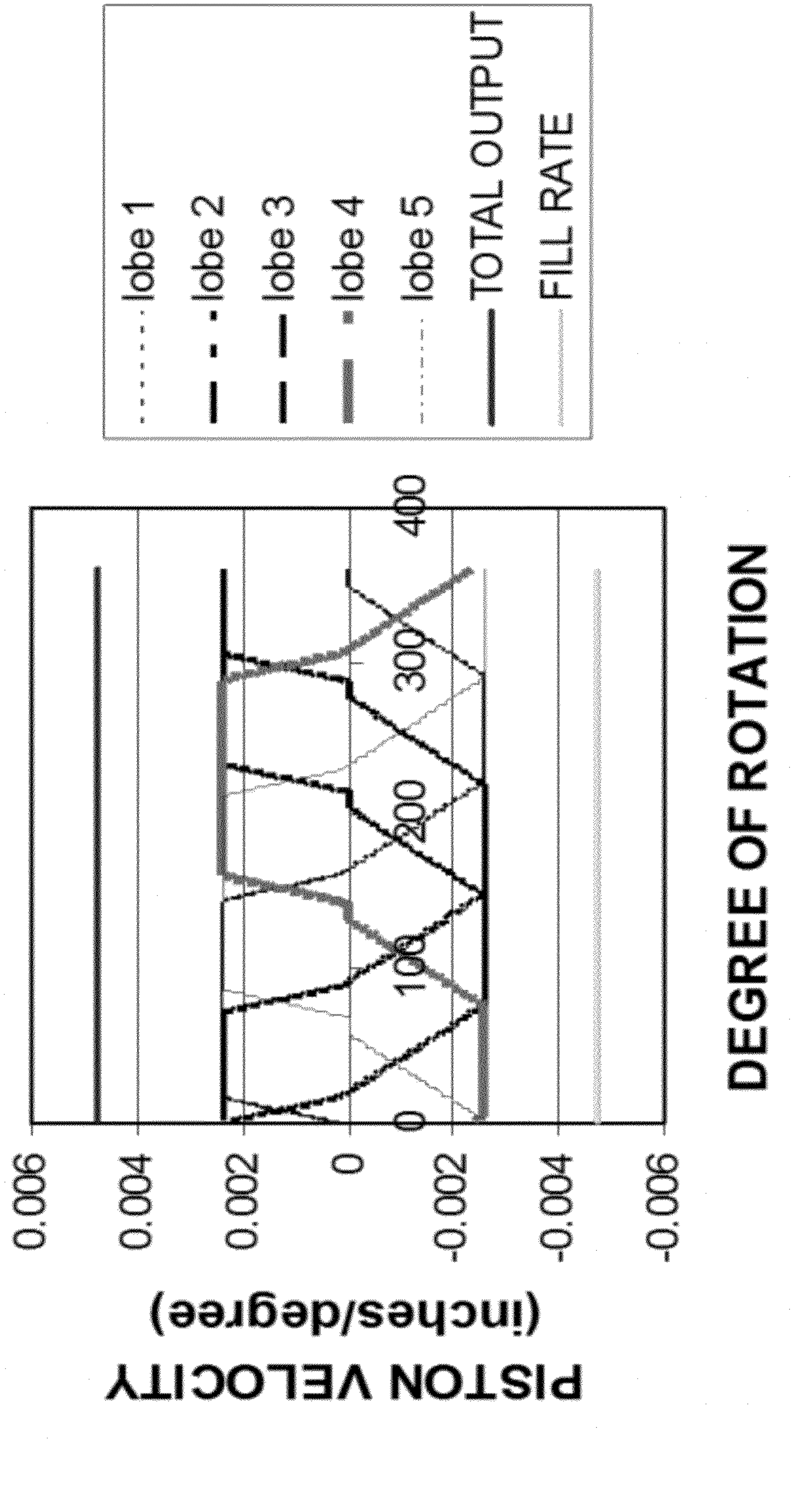

FIG. 2F illustrates a cam lifter/piston velocity for each chamber, theoretical total output, and theoretical fill rate for a pump including five cam lobes having the cam lobe profile of FIG. 2E.

FIG. 2G illustrates the measured pressure output from the five-cam pump of FIG. 2F.

Figure 2H:
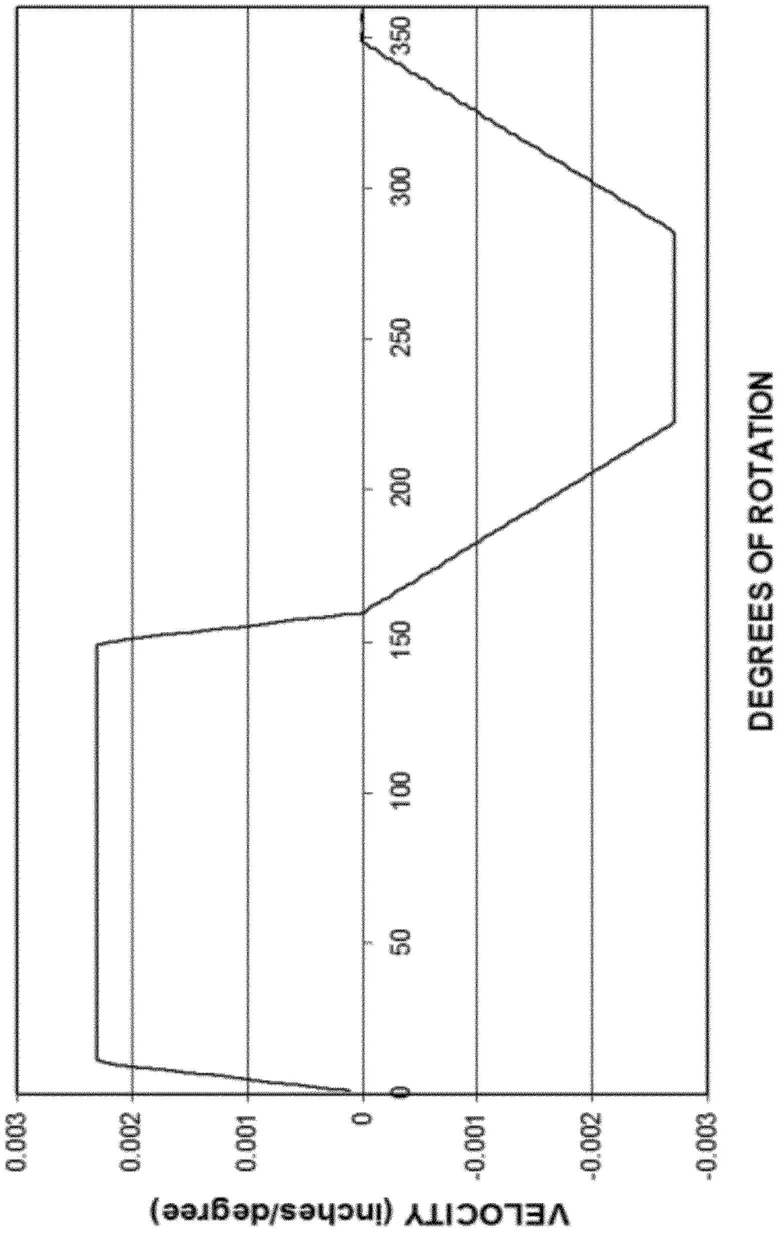

FIG. 2H illustrates cam lifter and/or piston velocity resulting from drive of a cam lifter/piston assembly via rotation of a cam lobe having a different cam lobe profile from that of FIG. 2E.

Figure 2I:
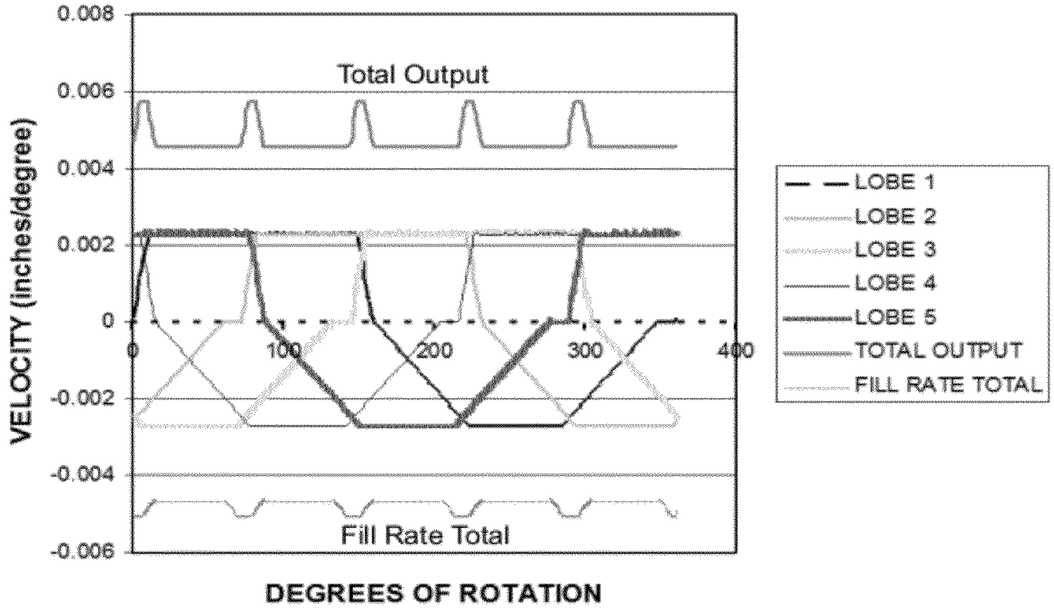

FIG. 2I illustrates a cam lifter/piston velocity for each chamber, theoretical total output, and theoretical fill rate for a pump including five cam lobes having the cam lobe profile of FIG. 2H.

Figure 2J:
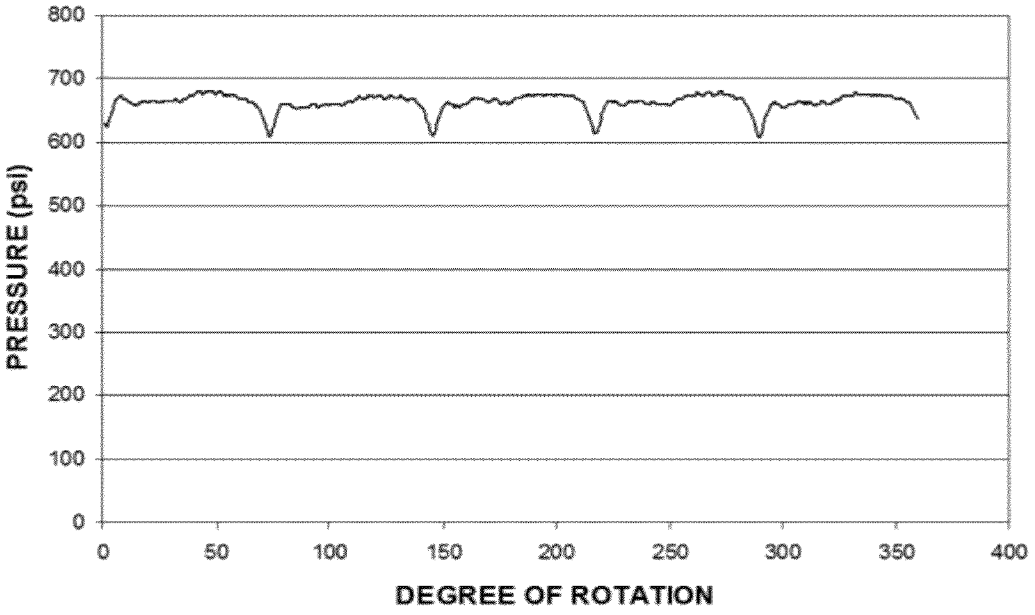

FIG. 2J illustrates the measured pressure output from the five-cam pump of FIG. 2I.

Figure 3A:
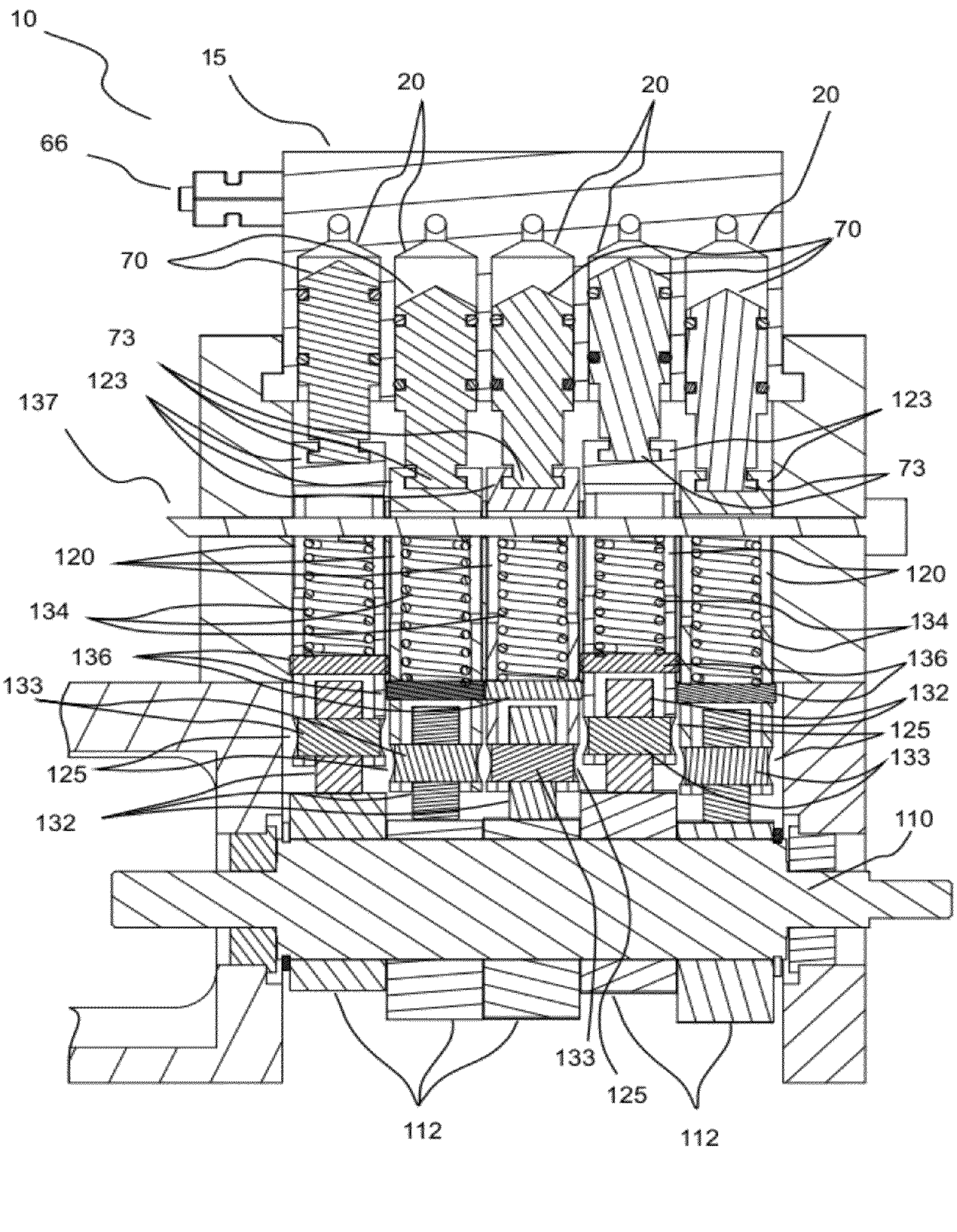

FIG. 3A illustrates a cross-sectional view of the pump system of FIG. 2A.

Figure 3B:
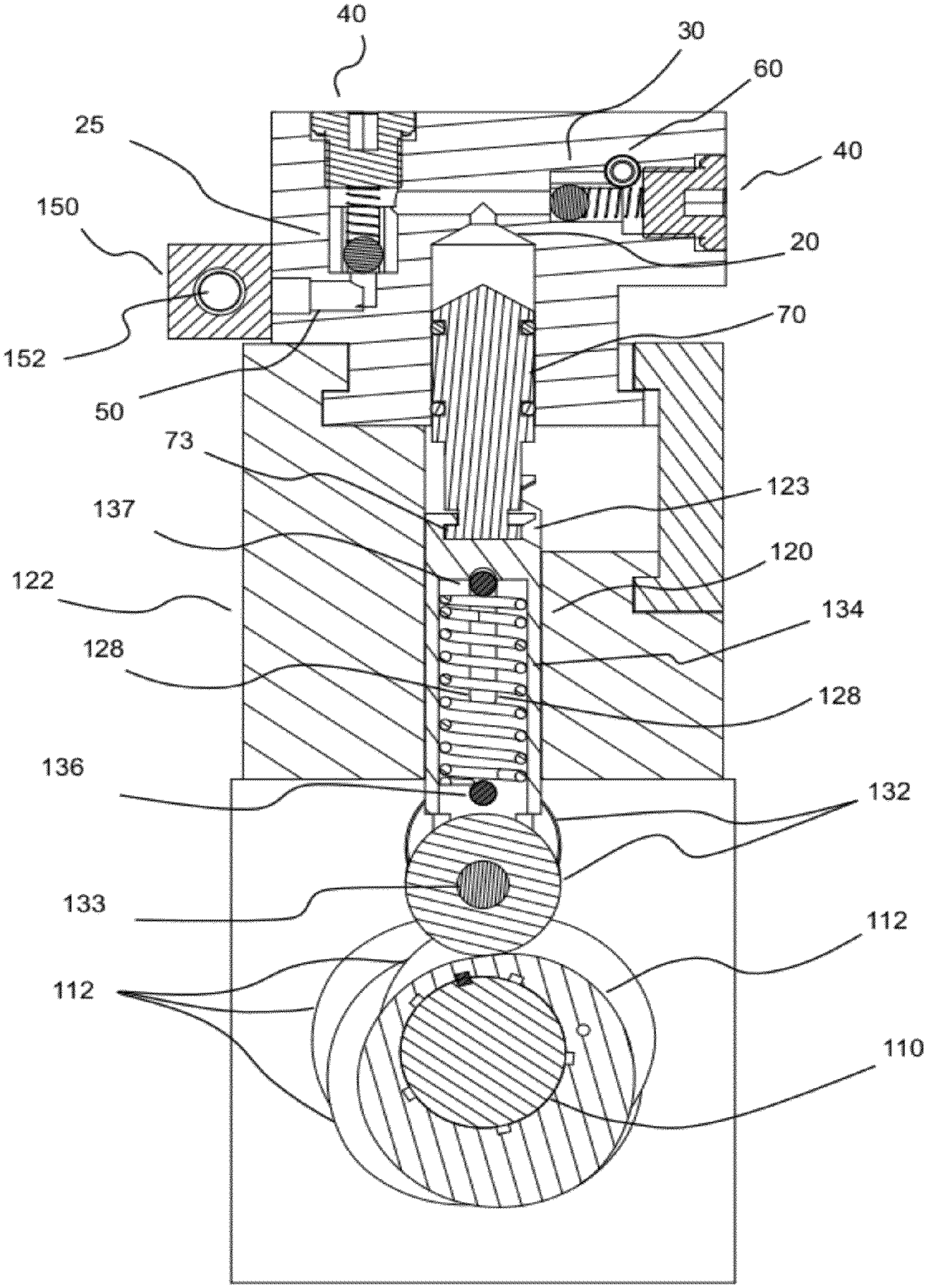

FIG. 3B illustrates another cross-sectional view of the pump system of FIG. 2A.

Figure 3D:
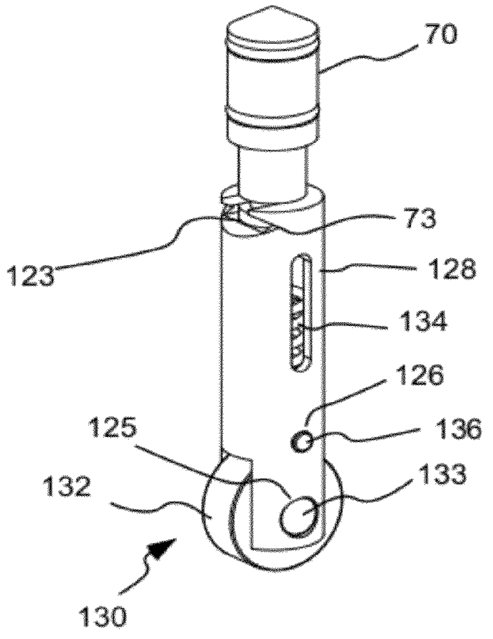
Figure 3E:
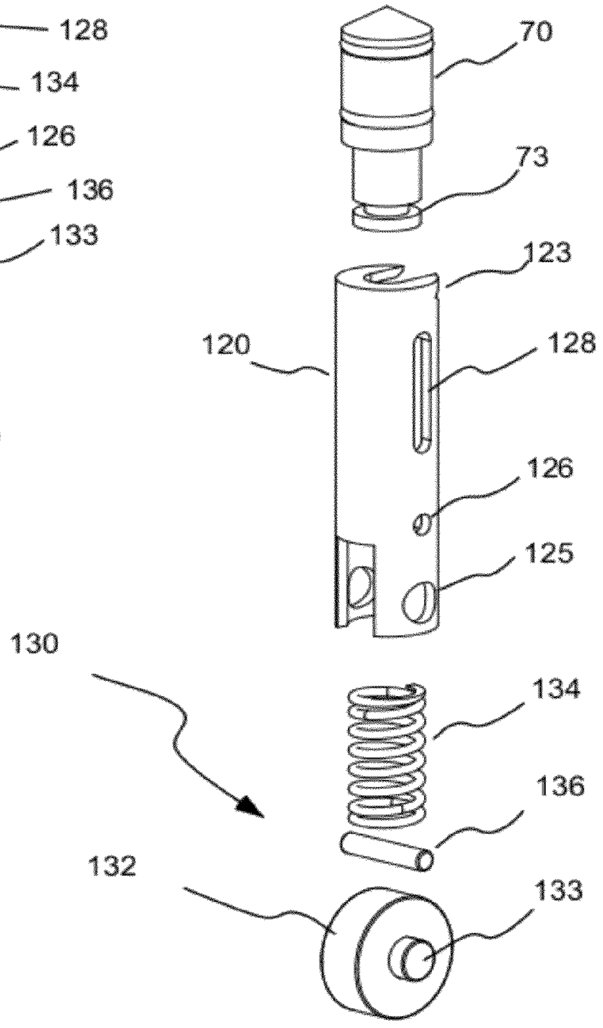
Figure 3C:
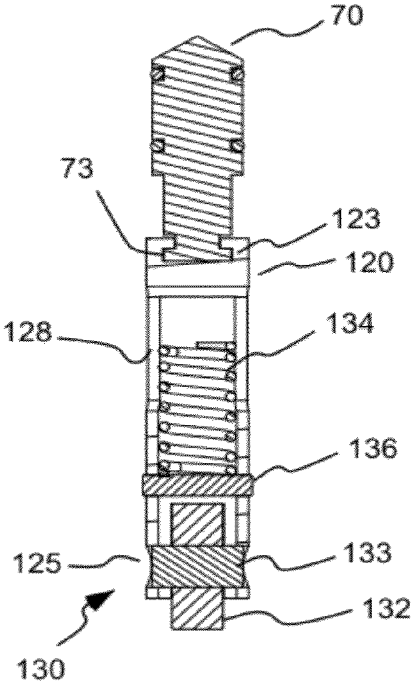

FIG. 3C illustrates a cross-sectional view of a piston and cam-follower assembly of the pump system of FIG. 2A, removed from connection with the remainder of the pump system.

FIG. 3D illustrates a perspective view of the piston and cam-follower assembly of FIG. 3C.

FIG. 3E illustrates an exploded, perspective view of the piston and cam-follower assembly of FIG. 3C.

Figure 1A:
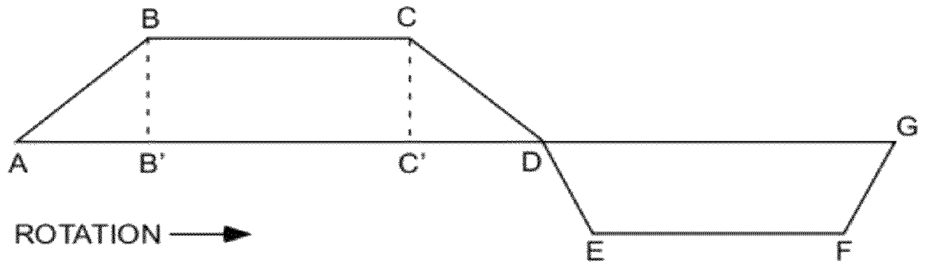
FIG. 1A illustrates cam lifter and/or piston velocity resulting from drive of a cam lifter/piston assembly via rotation of a cam lobe having a certain cam lobe profile.

FIG. 4A illustrates a perspective view of the cam shaft of the pump system of FIG. 1A.

FIG. 4B illustrates another perspective view of the cam shaft of the pump system of FIG. 1A.

FIG. 4C illustrates perspective views of each of the cam elements of the cam shaft of FIG. 4A, after removal of the cam elements from connection with the shaft.

Figure 5A:
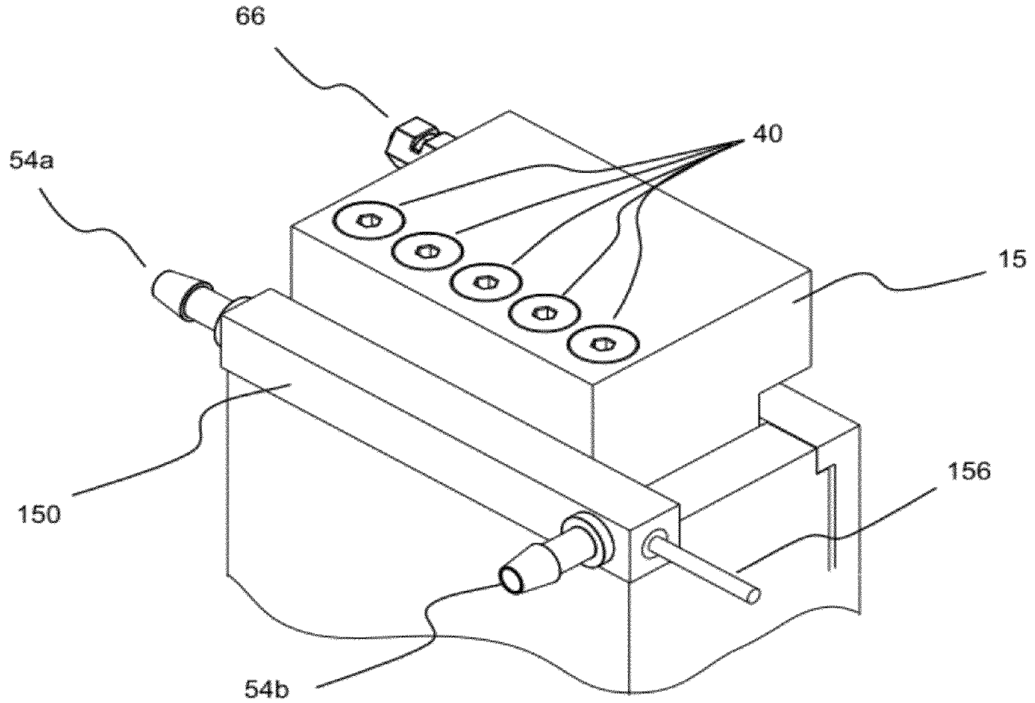

FIG. 5A illustrates an enlarged, perspective view of a portion of the pump system of FIG. 2A, illustrating an embodiment of a fluid intake system to vary the volumetric ratio of two fluids delivered to the pump.

Figure 5B:
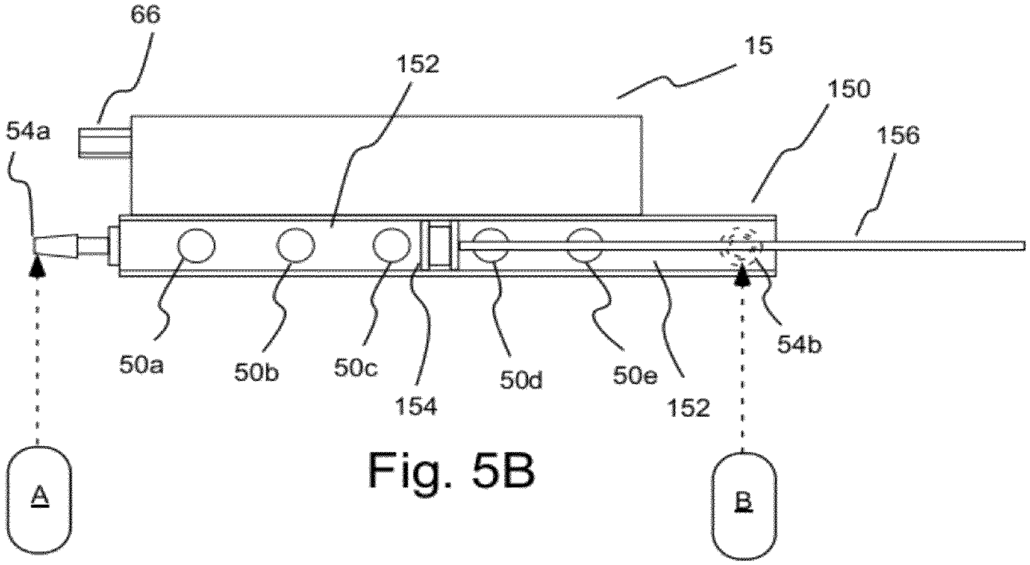

FIG. 5B illustrates a side, partially cutaway view of a portion of the pump system of FIG. 2A.

Figure 6A:
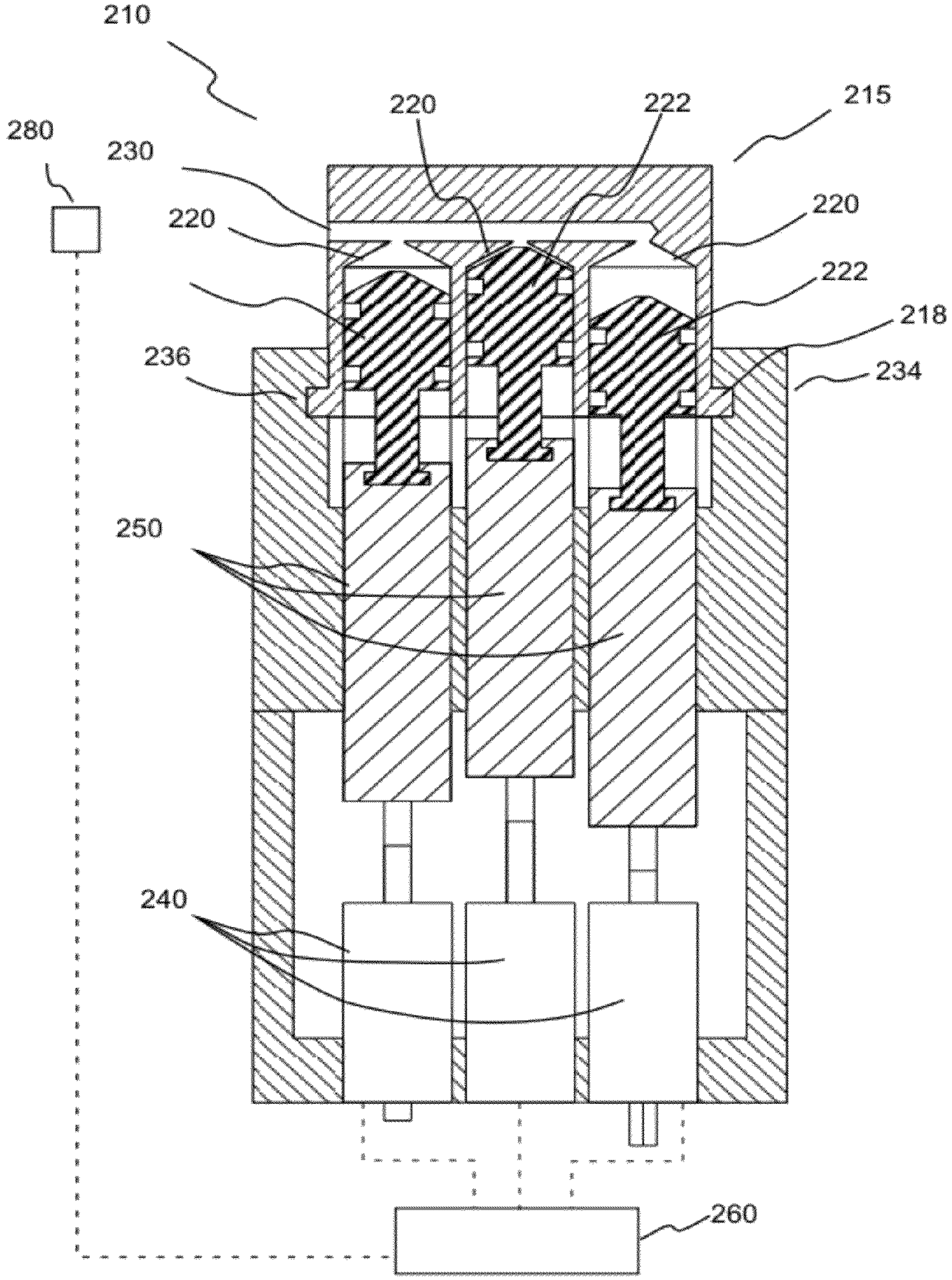

FIG. 6A illustrates a cross-sectional view of another embodiment of a pump system in which the drive of each piston is independently controllable.

Figure 6B:
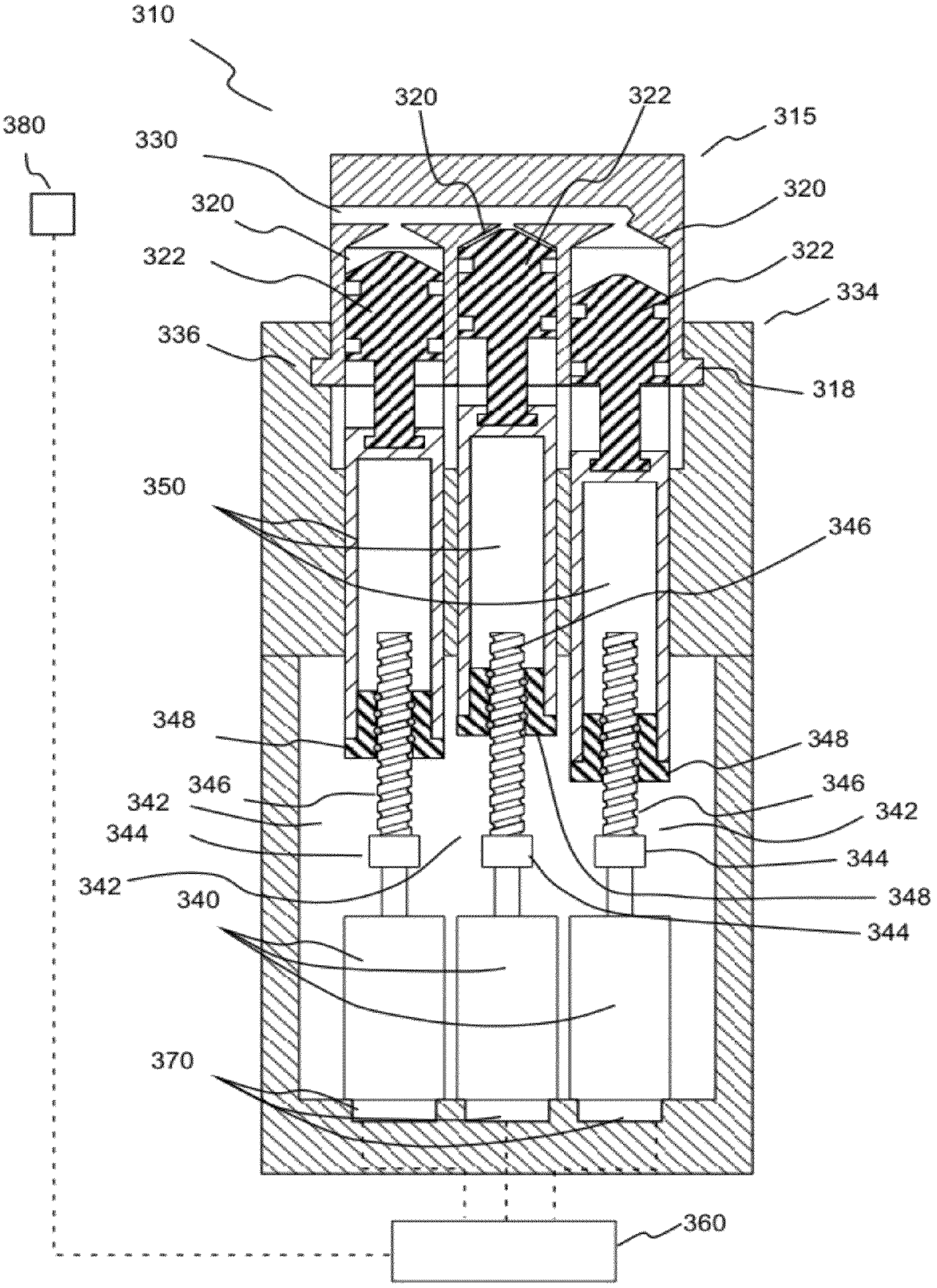

FIG. 6B illustrates a cross-sectional view of another embodiment of a pump system in which the drive of each piston is independently controllable.

DETAILED DESCRIPTION

As used herein and in the appended claims, the singular forms "a," "an", and "the" include plural references unless the content clearly dictates otherwise. Thus, for example, reference to "a check valve" includes a plurality of such check valves and equivalents thereof known to those skilled in the art, and so forth, and reference to "the check valve" is a reference to one or more such check valves and equivalents thereof known to those skilled in the art, and so forth.

The devices, systems and methods described herein can, for example, be used to pressurize medical fluids for injection into a patient over a pressure range of approximately 10 to 2000 psi (and more typically 25 to 1500 psi) and over a flow rate range of approximately 0 to 100 ml/sec (and more typically 0 to 50 ml/sec).

U.S. patent application Ser. No. 12/974,549 discloses a number of multi-cylinder, pumping devices, systems and methods for use with medical fluids. These include, for example, pumps having three chambers and pressurizing pistons disposed therein, which are in operative connection with a cam shaft to drive motion of the pressurizing pistons within the chambers. Various compensating systems are also disclosed to reduce pulsatility in flow.

Pulsatility can, for example, be measured in terms of variations in flow rate or variations in pressure. As set forth in U.S. Pat. Nos. 6,197,000 and 5,916,197, a degree or percent of pulsatile flow can be defined with the following equation:

$$100\%*(\text{max flow}-\text{min flow})/\text{average flow}$$

The standard deviation from an average pressure and/or flow rate can provide another or alternative measure of pulsatility. In general, pressure is more easily measured than flow rate.

In general, flow rate in the system is directly related to pressure change. In a simple system of flow of an incompressible fluid in a pipe, this direct relationship can be shown from the following equation, derived from the Bernoulli equation:

$$p_B = p_A - \rho g\left(\Delta z + f\frac{L}{D}\frac{V^2}{2g}\right)$$

wherein, $p_B$ is pressure at point B, $p_A$ is pressure at point A, ρ is fluid viscosity, g is the gravity acceleration constant, z is pipe elevation above some datum, f is a friction factor, D is pipe diameter, L is pipe length between point A and point B and V is the average velocity of the fluid. Likewise, for viscous, incompressible flow in a long pipe (that is, having a length significantly longer than its diameter) of circular cross-section, the Hagen-Pouiseulle equation provides $$Q = \int_0^R 2\pi v_z\, dr = \frac{\pi R^4}{8\mu}\frac{\Delta p}{L}$$

wherein Q is volumetric flow rate, R is the radius of the pipe, μ is dynamic fluid viscosity, L is the length of the pipe and Δp is the pressure change. Although there is no corresponding simple equation to provide flow rate as a function of pressure in a pump system, the above equations are indicative of the direct relationship between flow rate and pressure (for example, as measured in outlet conduit 60 of an outlet 64) in a pump system.

A number of multi-chamber or multi-cylinder pump systems were designed to deliver continuous flow with minimal pulsatility. For example, cam shafts and associated cam lobes were designed to provide theoretically constant pressures/flows, and other components were selected to provide the best output. However pulsatility remained in the flow. As described above, the fluid output associated with a number of cams shaft lobes should theoretically have been constant for a constant rotational velocity of the cam shaft. As the pressure rises, however, and without limitation to any mechanism, it is believed that mechanical capacitance (for example, compression and stretch of components under load) causes delays in the rise of pressure associated with individual pistons. As the delay increases, the system fluid pressure drops in the region of overlap of output of the cylinders.

In a number of embodiments of pump systems hereof, the cam lobe profile was altered to reduce or minimize pulsatility. The cam lobe profiles in several representative embodiments of pump systems were based approximately upon that of an isosceles trapezoid (referring to the corresponding velocity profile for a cam lifter and/or piston in operative connection with the cam lobe) for fluid delivery and filling of the chambers. As used herein, the term "profile" of a cam lobe refers to the manner in which a radius, as measured from the center of a cam shaft about which the cam lobe rotates (see $r_c$ in FIG. 4C), varies around the circumference of the cam lobe. As the variance of radius $r_c$ determines the direction and velocity of a cam lifter and/or piston in operative connection with the cam lobe upon rotation of the cam lobe, the resultant velocity of the cam lifter and/or piston can be used to describe the cam profile. FIG. 1A, for example, illustrates the velocity of the cam lifter and/or piston upon rotation of a cam lobe. The velocity is proportional to the flow out of (during a fluid delivery phase) and into (during a fluid fill phase) one chamber of a pump system resulting from drive of a piston within the cylinder or chamber of the pump system via rotation of the cam lobe. The base line (line A-D-G) represents where there is no flow into or out of the cylinder of pump. Over the region A-D (the fluid delivery phase), the piston is advancing within the chamber, and fluid is being delivered. Over the region D-G (the fluid fill phase), the piston is being retracted within the cylinder and fluid is filling the chamber.

The area A-B-C-D is equal to the piston travel since it is the product of rotational distance and velocity. Also, the area D-E-F-G must have the same area as the fill area. The distance A-C is equal to 360 degrees divided by the number of cylinders. For example, for a three-cylinder pump, the distance A-C is 120 degree. For a five-cylinder pump, the distance A-C is 72 degrees. For an isosceles trapezoid distance, A-B' is equal to distance C'-D. Therefore, the average velocity is equal to the total stroke divided by A-C' or 120 degrees in the case of a three-cylinder pump. The acceleration (the area A-B-B') is the average velocity divided by the number of degrees that acceleration is desired (distance A-B'). The filling of the pump cylinder is determined in the same manner. However, the distance A-G cannot exceed 360 degrees.

One embodiment of a cam having a symmetric profile had the following specifications.

TABLE 1

| | |
|---|---|
| Total lift | 0.363 |
| Constant acceleration angle | 60 |
| Constant velocity angle | 60 |
| Constant deceleration angle | 60 |
| Constant velocity | 0.003025 |
| Constant acceleration | 5.04167E−05 |
| Velocity at end of acc | 0.003025 |
| Position at end of acceleration | 0.09075 |
| Position at end of const vel. | 0.27225 |
| Position at 180 | 0.363 |

Figure 1B:
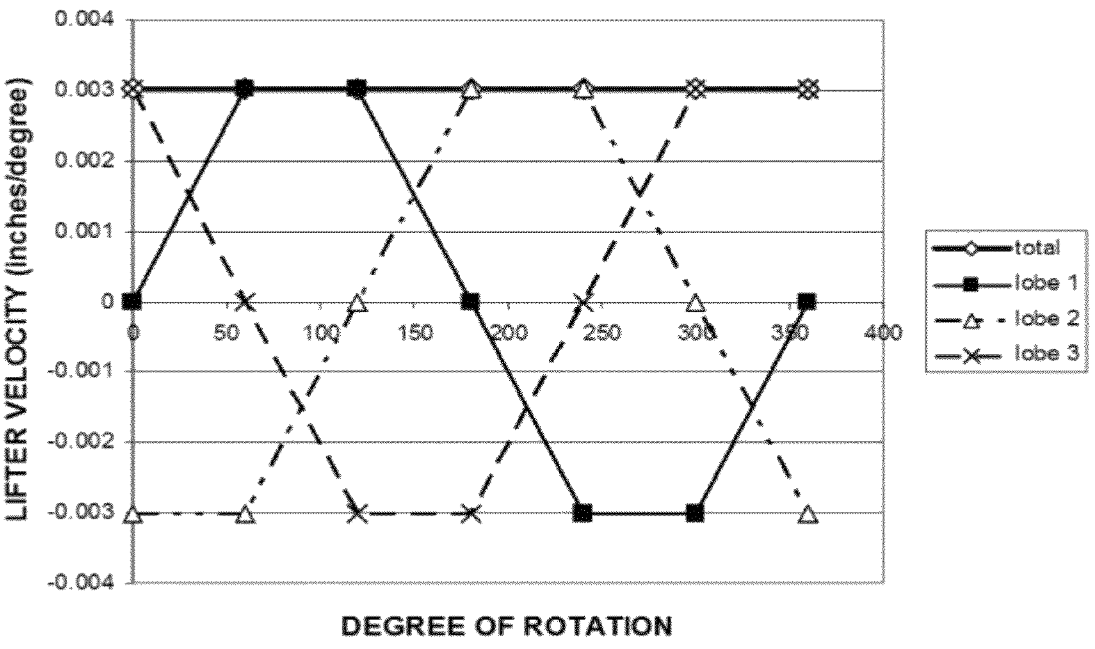
FIG. 1B illustrates a cam lifter/piston velocity, which is equivalent to theoretical flow velocity depending on the cam rotation speed, for a pump including three cam lobes having the cam lobe profile of FIG. 1A.
Figure 1C:
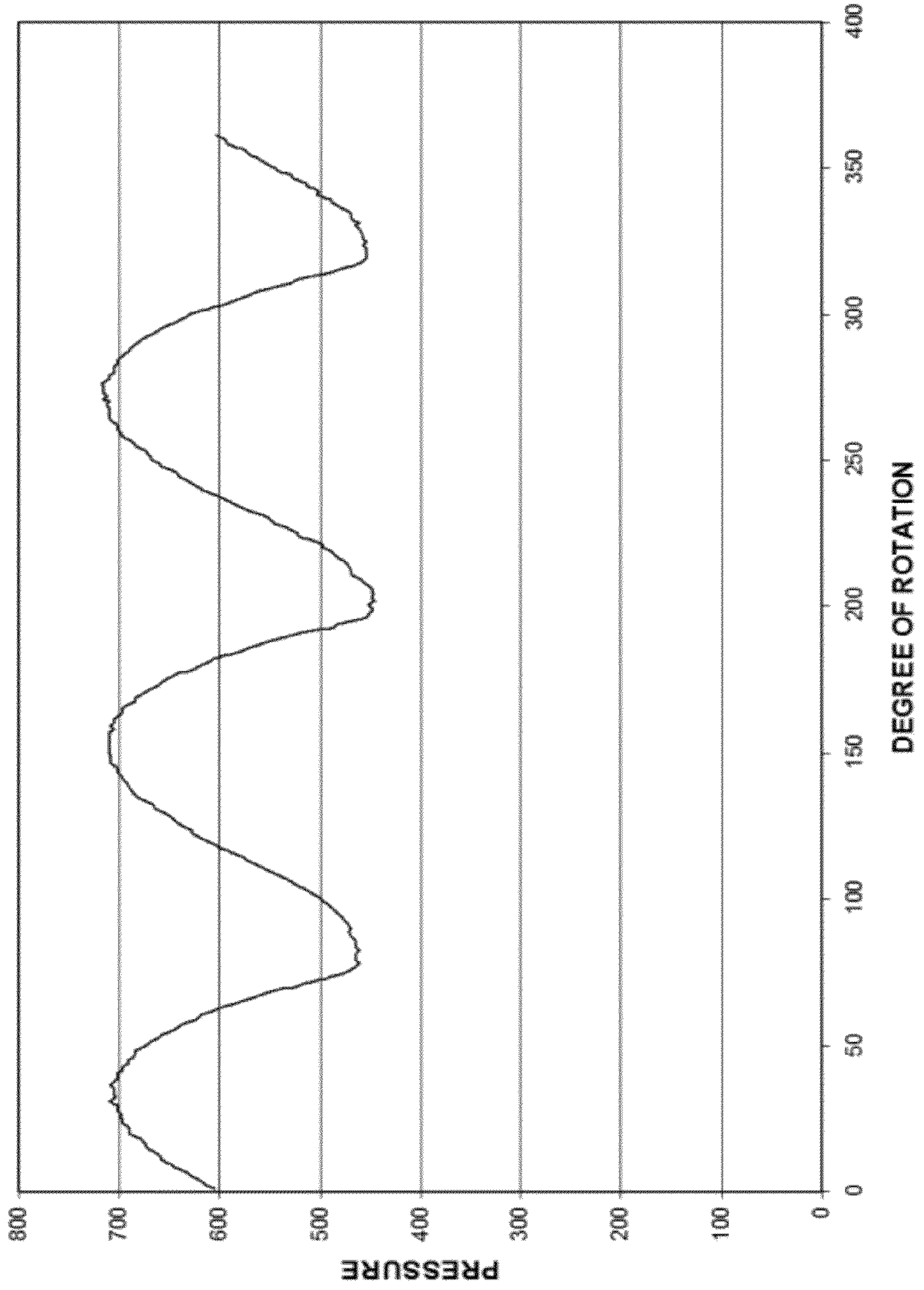
FIG. 1C illustrates the output (pressure as a function of degree of rotation) of a three-cam pump having the cam lobe profile of FIGS. 1A-1B and demonstrating substantial variation in pressure or pulsatility.

FIG. 1B illustrates the resultant cam lift profile. The information is equivalent to theoretical flow velocity depending on the cam rotation speed. FIG. 1C illustrates the output pressure as a function of degree of rotation for the pump at an average operating pressure of approximately 640 pounds per square inch (or psi). As illustrated in FIG. 1C, there was a significant drop in pressure at the point where one cam is accelerating and another cam is decelerating. A variation of almost a ±23% in pressure is exhibited.

Figure 1D:
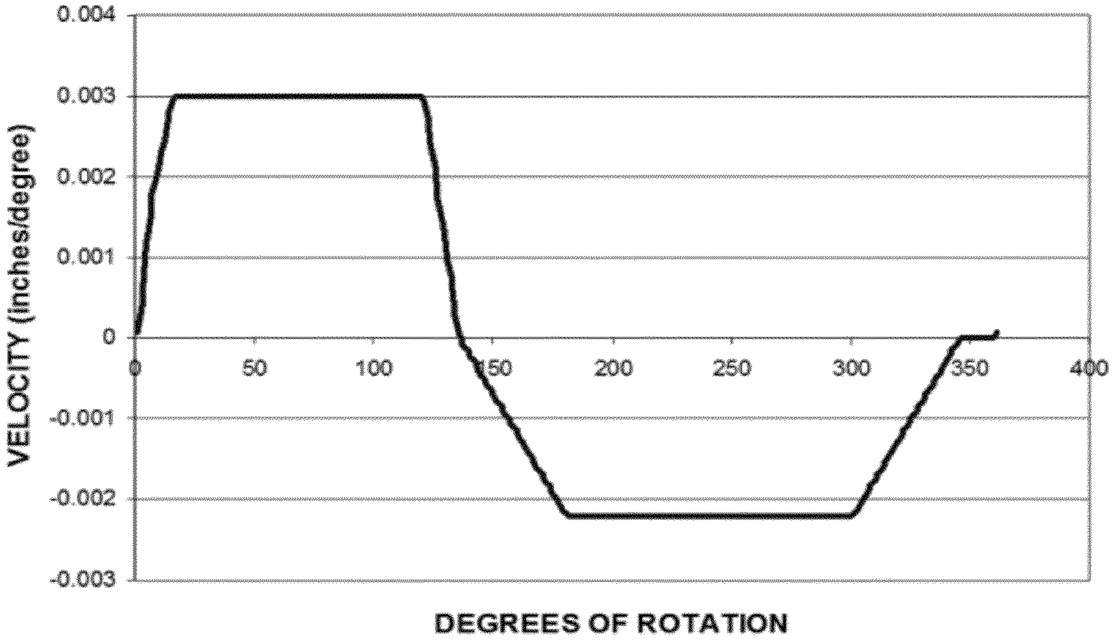
FIG. 1D illustrates piston velocity as a function of degree of rotation for a cam lobe designed to exhibit faster acceleration and make the constant velocity portion of the cam longer than the embodiment of FIG. 1A.
Figure 1E:
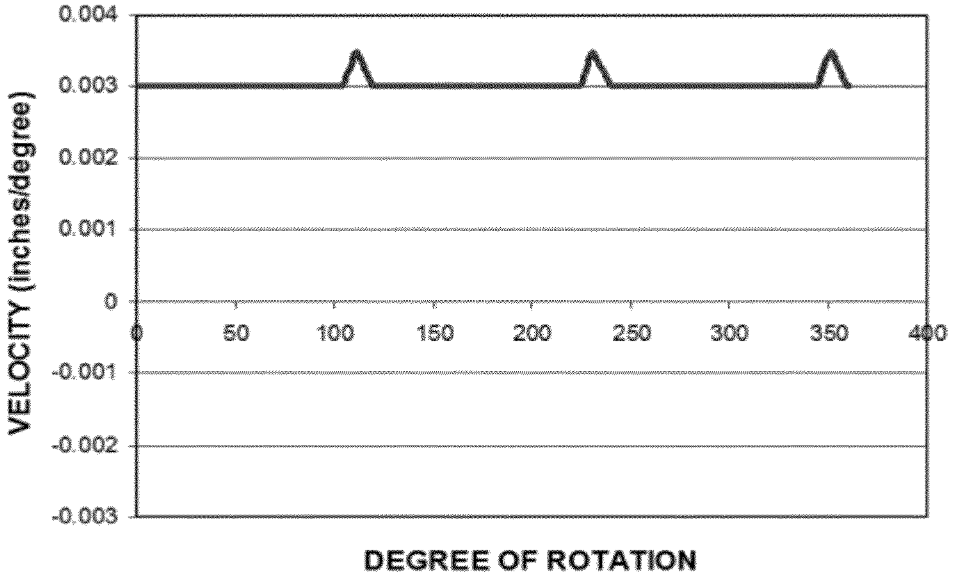
FIG. 1E illustrates a theoretical flow profile of a pump including three cam lobes as described in FIG. 1D.

To address such pressure variation or pulsatility, the cam lobes of the cam shaft were redesigned to make the constant velocity portion of the cam longer and the acceleration portions shorter. In one embodiment, and as illustrated in FIG. 1D, each cam lobe had a start (in the piston advance/fluid delivery portion) with an initial acceleration of 0.00029 inches/deg$^2$ for 7 degrees, then acceleration of 0.00014 inches/deg$^2$. This acceleration was followed by 103 degrees of constant velocity of 0.300 inches/degree. The deceleration was the reverse acceleration to 137 degrees. After 137 degrees the piston was retracting, (and the cylinder is filling). From 350 degrees to 360 degrees, the piston was in the fully down or retracted position, allowing for extra time for complete filling of the piston chamber. FIG. 1E illustrates the theoretical flow profile of the pump system with three cams as described above. The three peaks or periods of increased velocity/flow illustrated in FIG. 1E occur where the pressure drops occurred in the pump of FIG. 1C.

Figure 1F:
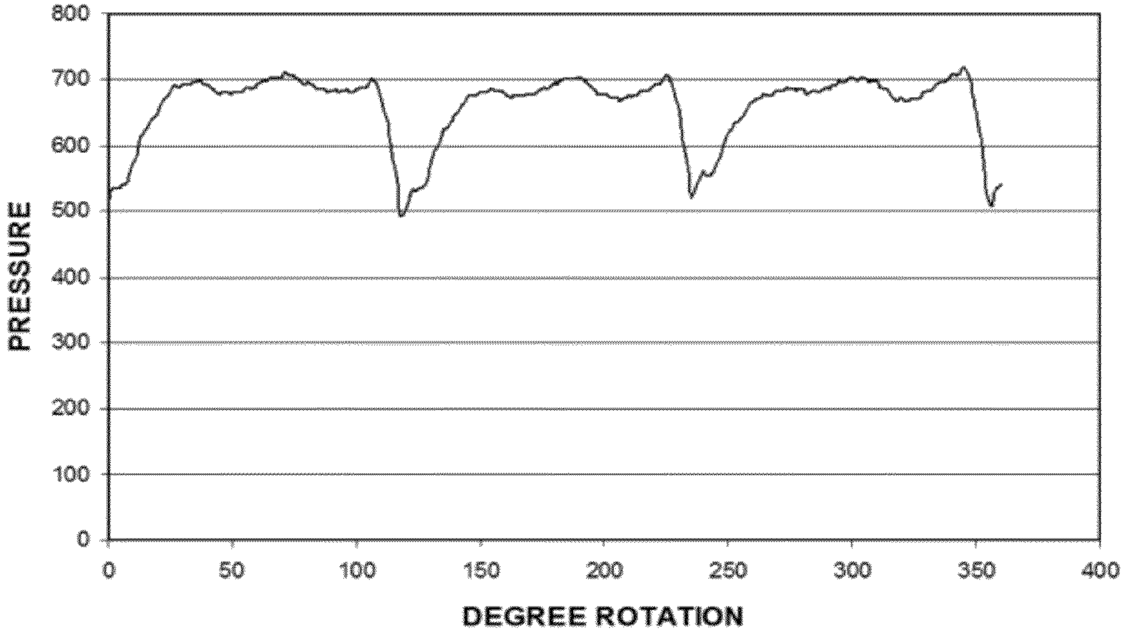
FIG. 1F illustrates the measured pressure output from the three-cam pump of FIG. 1E, showing the effect of the change to the cam lobe profile.
Figure 1G:
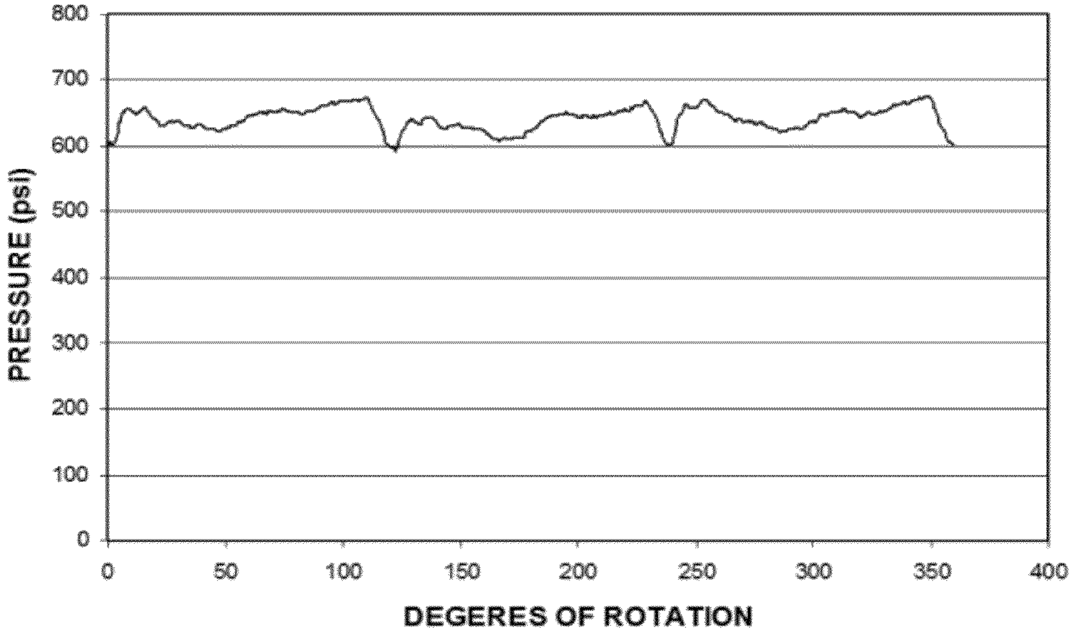
FIG. 1G illustrates the measured pressure output from the three-cam pump of FIG. 1E including both a compensating system as illustrated in FIG. 2A of U.S. patent application Ser.

FIG. 1F illustrates the pressure output from the three-cam pump system, showing the effect of the change to the cam profile. In that regard, a significant improvement in the pulsatility was achieved, with a pressure variation of approximately +7.5% and −25% or approximately ±16%. FIG. 1G illustrates the pressure output from such a three-cam pump system, but further including both a compensating system as illustrated in FIG. 2A of U.S. patent application Ser. No. 12/974,549 and a compensating system as described in FIG. 4A of U.S. patent application Ser. No. 12/974,549. The average pressure was 640 psi. and the pressure variation was approximately +5% and −8%.

FIGS. 2A through 3B illustrate another representative embodiment of a multi-cylinder pump system 10 including five cylinders or chambers. In the illustrated embodiment, five chambers or cylinders 20 (see, for example, FIG. 3A) of a pressurizing unit 15 are in generally linear, side-by-side alignment (that is, the axes of chambers 20 are generally in the same plane).

Each chamber 20 has an inlet port 25 and an outlet port 30 in fluid connection therewith (see, for example, FIG. 3B). Inlet ports 25 and outlet ports 30 can, for example, be provided with check valves or plug valves 40 to assist in maintaining the desired direction of flow. Inlet ports 25 are preferably in fluid connection with an inlet passage, conduit or channel 50, while outlet ports 30 are in fluid connection with a common outlet passage, conduit or channel 60.

In the illustrated embodiment (see, for example, FIG. 2A and 3B), and as further described below, each inlet channel 50 is in fluid connection with either or both of an inlet port 54*a* or an inlet port 54*b* (each of which, can for example, include a barbed connector) for attachment to a source A of a first fluid (such as a contrast medium or other pharmaceutical/medical fluid) or a source B of a second fluid (for example, a diluent such as a saline solution). Outlet channel 60 (see, for example, FIG. 3B) can, for example, be in fluid connection with an outlet port 64 (see, for example, FIG. 2B), which can, for example, be in fluid connection with a connector such as a Luer connector 66. Connector 66 can, for example, connect to a delivery set including tubing and a catheter to deliver fluid to a patient.

Disposed within each chamber 20 is a pressurizing member or piston 70 suitable to alternatively draw the liquid medium into chamber 20 upon a downward or rearward stroke thereof and to expel/pressurize the liquid medium, forcing the pressurized liquid medium into outlet channel 60, upon an upward or forward stroke thereof. Motive force is provided to pistons 70 by, for example, an external motor-driven (or otherwise powered) drive mechanism or drive system 100 (illustrated schematically in FIG. 2A) that imparts reciprocating linear motion to pistons 70. High pressures (for example, used in contrast medium injection in CT and angiographic procedures) in outlet channel 60 are possible with the proper choice of materials and wall thickness. One or more sealing members such as O-rings can be positioned between each piston 70 and the inner wall of chamber 20' (for example, within seating formed in pistons 70) to form a sealing engagement therewith.

In a number of representative embodiments of pump system 10 used in the studies hereof, the bore diameter of each chamber 20 was approximately 0.5 inches and the stroke length of pistons 70 was approximately 0.342 inches, resulting in a displacement of 5.5 ml per revolution of cam shaft 110 for pump system 10. The chambers and pistons of the pump systems hereof can, for example, be dimensioned and operated to provide a range of fluid displacements per revolution. In a number of embodiments, pump systems hereof exhibit a displacement per revolution in the range of approximately 1 to 10 ml.

As discussed above, drive mechanism 100 (illustrated schematically in broken lines in FIG. 2A) can, for example, be in inoperative connection with a timing mechanism, system or shaft such as a cam shaft 110 to drive pistons 70 in a timed sequence, which can be designed to reduce or minimize pulsatile flow. Drive mechanism 100 (for example, including an electric motor) is in operative connection with cam shaft 110. Cam elements or lobes 112 of cam shaft 110 can, for example, be in operative connection with cam lifter assemblies or piston extension members 120 which are reciprocally moveable through seatings formed in a lifter block 122 and terminate on one end thereof in attachment members which cooperate with corresponding attachment members on pistons 70. For example, retention slots 123 on piston extension members 120 can cooperate with flanges 73 (see, for example, FIG. 3A) on pistons 70 to form a readily releasable connection between pistons 70 and piston extension members 120.

FIG. 2E illustrates piston/lifter velocity versus degree of rotation for one embodiment of cam lobes 112 of pump system 10. During the fluid delivery phase, the embodiment of FIG. 2E exhibited an area of acceleration of 0.000132 inches/degree$^2$ for 18 degrees, then a constant velocity of 0.002359 inches/degree for 126 degrees, and then a deceleration of 0.000132 inches/degree$^2$ for 18 degrees. During the fluid fill phase, the embodiment of FIG. 2E exhibited an acceleration of 0.0000444 inches/degree$^2$ (down) for 59 degrees. then a constant velocity of 0.00263inches/degree for 71 degrees (down), and then a deceleration of 0.0000444 inches/degree$^2$ for 58 degrees to the bottom of the stroke. A stationery position followed for 10 degrees to guarantee filling.

Unlike a three-cylinder pump system, in the case of a five-chamber or five-cylinder pump system, such as pump system 10, there are always at least two cylinders that provide output or input at any time as seen, for example, in FIG. 2F which illustrates the output for each chamber and the total output of a five-chamber pump. Thus, the flow from a cylinder or chamber is at most half of the total output of the pump system at any point in time. When one piston 70 of a chamber 20 is accelerating, and another piston 70 of another chamber 20 is decelerating, a third piston 70 of a third chamber 20 is at full output and is delivering half of the desired flow. The crossover point is where a pressure drop typically occurs. In the case of a five-chamber pump system, the pressure drop should be half as much as in the three-chamber pump system.

As illustrated in FIG. 2G, which sets forth the outlet pressure of pump system 10 as a function of the degree of pump rotation, pump system 10, with the cam lobe design of FIG. 2E, showed an improvement over the three-chamber pumps discussed above. FIG. 2G illustrates an average pressure of 693 psi with a pressure variation of +5.4% and −14%. However, there was more variation than the three-chamber pump which included a compensating system as illustrated in FIG. 2A of U.S. patent application Ser. No. 12/974,549 and a compensating system as described in FIG. 4A of U.S. patent application Ser. No. 12/974,549.

Another embodiment of a cam lobe profile for five-chamber pump system 10 is illustrated in FIG. 2H, which sets forth the velocity of the cam lifter/piston as a function of the degree of rotation. This cam lobe had a similar profile to that described in connection with FIG. 2E, but exhibited an increase in acceleration and deceleration as compared to the embodiment of FIG. 2E so that the impact of the crossover was decreased. In the fluid delivery/forward piston movement phase, the cam lobe profile of FIG. 2H exhibited an acceleration of 0.000295 inches/degree$^2$ for 10 degrees, then a constant velocity of 0.002295 inches/degree for 139 degrees, and then a constant deceleration of 0.000295 inches/degree$^2$ for 10 degrees. In the chamber fill/reverse piston movement phase, the cam lobe profile of FIG. 2H exhibited a constant deceleration of 0.000042 inchs/degree$^2$ for 65 degrees, then a constant velocity of 0.0027 inches/degree for 61 degrees, and then an acceleration to the bottom of the stroke of 0.00004175 inches/degree$^2$ for 65 degrees. A 10-degree dwell at the bottom of the stroke followed to provide additional fill time.

For a mathematically or theoretically uniform flow with this type of cam lobe profile, the constant velocity section would extend to 144 degrees, rather than to 149 degrees as described above. Extending the constant velocity section or portion by five extra degrees reduces or minimizes the pressure drop as compared to that exhibited by the cam lobe design of FIG. 2E. Because of the 5 degrees of overlap, there are peaks in the theoretical total output as illustrated in FIG. 2I. The peaks are designed to counteract the periodic pressure drops illustrated in FIG. 2G. As illustrated in FIG. 2I, operation of pump system 10 with such cam lobe profiles at an average pressure to be 631 psi resulted in a pressure variation of approximately +2.8% and −8.5%. Thus, five-chamber pump system 10 provides similar performance to the three-chamber pump system of U.S. patent application Ser. No. 12/974,549 which includes both compensating systems as illustrated in FIGS. 2A and FIG. 4A without the requirement of additional compensating systems. However, such compensating systems can be used in connection with pump system 10 of the present disclosure to even further reduce pulsatility.

Piston extension members or cam lifters 120 can, for example, be placed in operative connection with cam shaft lobes 112 via cam follower assemblies 130. In the illustrated embodiment, cam follower assemblies 130 include a bearing member or cam bearing 132 which is attached to cam lifter 120 via extending members or bearing axle members 133 which pass through passages 125 in cam lifters 120. In the illustrated embodiment (see FIGS. 3C-3E), cam follower assembly 130 includes a biasing element such as a spring 134 which is retained within an interior cavity of generally cylindrical cam lifters 120. In the illustrated embodiment, spring 134 is retained between a first abutment element (including, for example, a pin 136, which passes through passages 126 in cam lifters 120) and a second abutment member 137 (including, for example, a pin or connector 137 (see, for example, FIGS. 3A and 3B) which passes through a passage 121 in lifter block 122 and through extending slots 128 formed in each of piston extensions 120). Spring 134 ensures that bearing member 132 remains in contact with the corresponding cam lobe 112 and thus that piston 70 is drawn rearward within chamber 20 as the radius of that portion of cam lobe 112 in contact with bearing member 132 reduces (upon rotation of cam shaft 110; see, for example, FIG. 3A). Further, fluid pressure from inlets 54*a* or 54*b* will not cause flow of fluid through pump system 10. Fluid will flow through pump system 10 only upon rotation of cam shaft 110 via powered drive 100.

In the assembly of cam lifters 120 and cam follower assemblies 130, spring 134 is inserted into the body of cam lifter 120. Spring 134 is partially compressed and held in place by insertion of spring retaining pin 136. The bearing and axle are then attached. Lifters 120 are inserted into the body or lifter block 122 of pump 10. When all cam lifters 120 are inserted within lifter block 122, a retaining and anti-rotation device such as pin 137 is installed. Pin 137 is inserted into slot 128 on the side of cam lifters 120 so that there is free movement up and down in slot 128 but pin 137 prevents rotation of cam lifters 120 within block 122, facilitating the tracking or following of cam lobes 112 by cam follower bearings 132. Spring 134 is captured between retaining pin 136 and anti-rotation pin or connector 137. As rotation of cam lobe 112 moves cam lifter 120 upward (in the orientation of the figures), spring 134 is compressed. When the profile/radius $r_c$ (see FIG. 4C) of cam lobe 112 drops or decreases, spring 134 applies force to cam lifter 120 to move cam lifter 120 downward (in the orientation of the figures) so that cam follower bearing 132 remains in contact with and follows the profile of associated cam lobe 112. If cam follower bearing 132 did not maintain contact with cam lobe 112, piston 70 would not be pulled or retracted to its lowest (in the orientation of the figures) position and an incomplete fill of chamber 120 would occur, resulting in a decrease in pump output.

Pressurizing unit 15 can, for example, be placed in operative connection with lifter block 122 via a flange 18 which can be seated in a seating 124 (see FIG. 2B). In this manner, the fluid contacting portions of system 10, including pressurizing unit 15 can be readily removed from connection with drive mechanism 100. Pressurizing unit 15 can be disposable (for example, on a per-patient, per time or other basis) to, for example, reduce or eliminate the risk of cross-patient contamination. Pressurizing unit 15 can, for example, be formed relatively inexpensively from polymeric, metallic, ceramic and/or other materials by any number of processes including, molding, injection molding, coinjection molding, extrusion, machining, etc.

In the illustrated embodiments, inlets 54*a* and 54*b* are in fluid connection with a manifold or fluid distribution system 150, which includes a conduit or channel 152 therein (see FIG. 5B). Channel 152 is in fluid connection with ports 50*a* through 50*e*, which are in fluid connection with inlet channel 50. A sealing member 154 is slidably positioned within channel 152. The position of sealing member 154 can, for example, be controlled by control member 156. Control member 156 can, for example, be an extending member to which force is applied (manually or in an automatic or semi-automatic manner) to slide sealing member 154 within channel 152 (see, for example, FIGS. 5A and 5B).

As illustrated, for example, in FIG. 5B, the position of sealing member 154 in conduit can be used to control the amount of (or ratio of) fluid A and fluid B entering pressurizing unit 15. In FIG. 5B, sealing member 154 is positioned so that three ports (ports 50*a*, 50*b* and 50*c*) are in fluid connection with fluid source A, while two ports (ports 50*d* and 50*e*) are in fluid connection with fluid source B. If fluid source A and fluid source B are at approximately the same pressure and of approximately the same viscosity, the fluid entering pressurizing unit 15 (and exiting pressurizing unit 15) will include approximately 60% by volume fluid A and approximately 40% fluid B. In the embodiment of FIGS. 5A and FIG. 5B, the relative amounts of fluids A and B can be varied in approximately 20% increments by the positioning of sealing member 154 between ports 50*a* through 50*c*. The varying of the fluid ratios can, for example, be adjusted via a number of variables including, for example, the number and dimensions of the one or more fluid ports in fluid connection with channel 152.

In the systems describe above, a plurality of pistons are controlled by cams that are fixed to a common shaft. Testing of cam-driven pumps has shown that pulsatility or the degree of pulsatility changes as a function of flow rate and pressure. In the cam-driven systems described above, cams and systems associated therewith are designed to reduce this effect.

Alternatively, one of, a plurality of or all of the drives or pistons can be controlled independently in, for example, its timing, velocity, and position. In such an individually controlled piston pump, the piston acceleration and velocities can, for example, be optimized for the conditions experienced at a certain time. For example, the start-up of a piston can be advanced in time relative to the previously actuated piston, thereby beginning pressurization resulting from the piston sooner to reduce or prevent a pressure drop between pistons (as, for example, illustrated in the pressure waveforms described above in certain cam-driven systems).

In a number of embodiments, an independently controlled drive is provided for each piston of a pump system. Such a pump can, for example, have as few as two pistons. However a two-piston pump system has a disadvantage in that the fill time must be shorter than the pressurization portion of the piston cycle. In light of this disadvantage, three or more pistons/cylinders provide an advantage.

Each of the pistons can, for example, have a computer controlled drive in operative connection therewith. Such drives can, for example, be linear motors. A linear motor is an electric motor in which the stator is unrolled so that, rather than producing torque associated with rotation, the motor produces a linear force along its length. Alternatively, a traditional or standard motor can be used in connection with a linear drive (that is, a rotary-to-linear drive system).

Determination of individual piston control for a pump system can, for example, be based on running parameters such as total flow output and pressure. For example, a lookup table or chart or an algorithm can be stored in memory for access by a processor to, for example, set timing and individual piston velocities to achieve a desired goal of non-pulsatile flow.

Furthermore, additional feedback data or information can be provided to the processor from one or more sensors (for example, output pressure as measured by a pressure transducer) to effect control in the manner of a servomechanism. The system can, for example, anticipate required needs and use servo feedback to fine tune or adjust the system variables or parameters to achieve a desired result of flow with little or no pulsatility. Control inputs can, for example, include piston position, piston velocity, force on a piston, total flow output (as, for example, measured by a flow meter), output pressure (as, for example, measured by a pressure transducer), and individual chamber pressure (as, for example, measured by pressure transducers).

FIG. 6A illustrate a pump system 210 including independent control of each of a plurality of pistons 222 (three, in the illustrated embodiment) reciprocally movable or slidable within three piston chambers 220. Piston chambers 220 are in fluid connection with a common outlet channel 230. In the illustrated embodiment, each of pistons 222 is in operative connection with an independently controllable linear drive motor or linear motor 240 via a lifter or piston extension member 250. Each linear motor 240 independently controls a piston 222 operatively connected thereto. Linear motors 240 can, for example, be controlled by a control system 260 that, for example, regulates the velocity and positions of pistons 222. Control system 260 can, for example, include one or more computer processors. The output and the filling of each piston 222 cylinder 220 pair can, for example, be controlled throughout each cycle. One or more sensors 280 (for example, one or more pressure sensors and/or flow sensors) can, for example, be placed in connection with pump system 210 (for example, in connection with outlet channel 230 or in connection with the each of chambers 220) to provide feedback to control system 260 to effect independent control of each of pistons 222.

Similar to the pump systems described above, pump system 210 can include a pressurizing unit 215 that can, for example, be placed in operative connection with lifter block 234 via a flange 218 which can be seated in a seating 236. In this manner, the fluid contacting portions of system 210, including pressurizing unit 215, can be readily removed from connection with the drive mechanism as described above.

FIG. 6B illustrates a pump system 310 including independent control of each of a plurality of pistons 322 (three, in the illustrated embodiment) reciprocally movable or slidable within three piston chambers 320. Similar to pump system 210, piston chambers 320 are in fluid connection with a common outlet channel 330. In the illustrated embodiment, each of pistons 322 is in operative connection with an independently controllable rotary motor 340, which drives a linear drive 342 such as a ball screw or rack and pinion via a lifter or piston extension member 350. In the illustrated embodiment, each linear drive 342 is a ball screw including a coupler 344 to connect a ball screw 346 to each motor 340 (for example, a servo motor). Each ball screw 346 cooperates with a ball nut 348 connected to a rearward end of a piston extension member 350.

Each motor 340 independently controls a piston 322 operatively connected thereto. As described above, motors 340 can, for example, be controlled by a control system 360 that, for example, regulates the velocity and position of each of pistons 322. Control system 360 can, for example, include one or more computer processors. The output and the filling of each piston 322/cylinder 320 pair can, for example, be controlled throughout each cycle. Rotary encoders 370 can, for example, be operatively connected to motors 340 to assist in effecting control thereof. One or more sensors 380 (for example, one or more pressure sensors and/or flow sensors) can, for example, be placed in connection with pump system 310 (for example, in connection with outlet channel 330 or in connection with the each of chambers 320) to provide feedback to control system 360 to effect independent control of each of pistons 322.

Similar to the pump system 210, pump system 310 can include a pressurizing unit 315 that can, for example, be placed in operative connection with lifter block 334 via a flange 318 which can be seated in a seating 336. In this manner, the fluid contacting portions of system 310, including pressurizing unit 315, can be readily removed from connection with the drive mechanism as described above.

The foregoing description and accompanying drawings set forth embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A system for delivery of a medical fluid to a patient, the system comprising:

a pump system comprising:

a plurality of at least three chambers, each of the plurality of chambers comprising an inlet through which fluid is drawn into each of the chambers and an outlet from which fluid is expelled from each of the chambers;

a fluid intake system in fluid connection with the inlets of the plurality of at least three chambers, the fluid intake system comprising at least two fluid inlet ports, a control member to adjust the volumetric ratio of fluid delivered from the fluid inlet ports, and an extending channel in fluid connection with each of the fluid inlet ports, wherein the fluid inlet ports are spaced along the extending channel, and the control member comprises a sealing member in sealing engagement with the channel, the sealing member being movable within the channel to adjust the volumetric ratio;

a common outlet channel in fluid communication with the outlet of each of the plurality of chambers; and a plurality of at least three pistons, each of which is slidably disposed within a respective one of the plurality of chambers; and a drive system comprising:

a cam shaft comprising a plurality of at least three cam lobes, each of the plurality of cam lobes having a profile; and a plurality of at least three cam lobe followers, each of which is in operative connection with a respective one of the plurality of cam lobes and is adapted to be placed in operative connection with a respective one of the plurality of pistons;

wherein the profile of each of the plurality of cam lobes is adapted to provide a positive spike in calculated theoretical output of the pump system to reduce periodic variation in measured output thereof.

2. The system of claim 1 wherein the plurality of at least three chambers comprises five chambers, the plurality of at least three pistons comprises five pistons, the plurality of at least three cam lobes comprises five cam lobes, and the plurality of at least three cam lobe followers comprises five cam lobe followers.

3. The system of claim 2 wherein the profile of each of the cam lobes comprises a fluid delivery phase comprising an acceleration portion, a constant velocity portion and a deceleration portion.

4. The system of claim 3, further comprising a plurality of five cam lifters each having a first end and a second end, wherein the first end of each of the cam lifters is in removable connection with a respective one of the five pistons and the second end of each of the cam lifters is connected to a respective one of the five cam lobe followers.

5. The system of claim 4 wherein each of the cam lifters is in operative connection with a biasing element to retain the connected cam lobe follower in contact with the associated cam lobe during a chamber filling phase of the cam lobe profile.

6. The system of claim 5 wherein the biasing element comprises a spring positioned within the cam lifter.

7. The system of claim 6, further comprising a first abutment member which passes through the five cam lifters through respective extending slots defined in each of the five cam lifters to limit rotation of each of the cam lifters about a longitudinal axis thereof, each of the cam lifters being movable relative to the first abutment member in the direction of the longitudinal axis of the cam lifter.

8. The system of claim 7 wherein each of the springs abuts the first abutment member at a first end of each of the springs and a second abutment member connected to the respective cam lifter at a second end of each of the springs.

9. The system of claim 1 wherein the fluid intake system further comprises a plurality of spaced outlet ports within the extending channel and in fluid connection with the extending channel and with the inlets of the plurality of chambers.

10. The system of claim 9, wherein the plurality of spaced outlet ports are positioned within the extending channel between positions of the at least two fluid inlet ports.

11. A system for delivery of a medical fluid to a patient, the system comprising:

a pump system comprising a plurality of at least three chambers, each of the plurality of chambers comprising a piston slidably disposed therein, an inlet through which fluid is drawn into each of the chambers, and an outlet from which fluid is expelled from each of the chambers, the outlet of each of the plurality of chambers being in fluid connection with a common outlet channel, a cam shaft comprising a plurality of at least three cam lobes, each of the plurality of pistons being in operative connection with one of the plurality of cam lobes via one of a plurality of at least three cam lobe followers; and a fluid intake system in fluid connection with the inlets of the plurality of chambers, the fluid intake system comprising at least two fluid inlet ports, a control member to adjust the volumetric ratio of fluid delivered from the fluid inlet ports, and an extending channel in fluid connection with each of the at least two fluid inlet ports of the fluid intake system, wherein the at least two fluid inlet ports are spaced along the extending channel and the control member comprises a sealing member in sealing engagement with the extending channel, and wherein the sealing member is movable within the extending channel between the at least two fluid inlet ports to adjust the volumetric ratio of fluid delivered from the fluid inlet ports.

12. The system of claim 11 wherein the fluid intake system further comprises a plurality of spaced outlet ports within the extending channel providing fluid connection between the extending channel and the inlets of each of the plurality of at least three chambers.

13. The system of claim 12, wherein the plurality of spaced outlet ports are positioned within the extending channel between the positions of the fluid inlet ports.

14. A system for delivery of a medical fluid to a patient, the system comprising:

a pump system comprising:

a plurality of at least three chambers, each of the plurality of chambers comprising an inlet through which fluid is drawn into each of the chambers and an outlet from which fluid is expelled from each of the chambers;

a common outlet channel in fluid communication with the outlet of each of the plurality of chambers; and a plurality of at least three pistons, each of which is slidably disposed within a respective one of the plurality of chambers; and a drive system comprising:

a cam shaft comprising a plurality of at least three cam lobes, each of the plurality of cam lobes having a profile;

a plurality of at least three cam lobe followers, each of which is in operative connection with a respective one of the plurality of cam lobes and is adapted to be placed in operative connection with a respective one of the plurality of pistons;

a plurality of at least three cam lifters, each having a first end and a second end wherein the first end of each of the cam lifters is in removable connection with a respective one of the plurality of at least three pistons and the second end of each of the cam lifters is connected to a respective one of the plurality of at least three cam lobe followers;

a plurality of at least three biasing elements, each in operative connection with a respective cam lifter to retain the connected cam lobe followers in contact with the associated cam lobe during a chamber filling phase of the cam lobe profile; and a first abutment member which passes through the plurality of at least three cam lifters through respective extending slots defined in each of the cam lifters to limit rotation of each of the cam lifters about a longitudinal axis thereof, and each of the cam lifters is movable relative to the first abutment member in the direction of the longitudinal axis of the cam lifter wherein the profile of each of the plurality of cam lobes comprise a fluid delivery phase comprising an acceleration portion, a constant velocity portion and a deceleration portion and are adapted to provide a positive spike in calculated theoretical output of the pump system to reduce periodic variation in measured output thereof.

15. The system of claim 14 wherein each of the biasing elements abuts the first abutment member at a first end of each of the biasing elements and a second abutment member connected to the respective cam lifter at a second end of each of the biasing elements.

* * * * *

UNITED STATES PATENT AND TRADEMARK OFFICE

CERTIFICATE OF CORRECTION

PATENT NO. : 8,944,780 B2
APPLICATION NO. : 13/071939
DATED : February 3, 2015
INVENTOR(S) : Reilly et al.

It is certified that error appears in the above-identified patent and that said Letters Patent is hereby corrected as shown below:

IN THE DRAWINGS:
In Fig. 1F, Sheet 4 of 18, delete "DEGREE ROTATION" and insert -- DEGREE OF ROTATION --, therefor.
In Fig. 1G, Sheet 4 of 18, delete "DEGERES" and insert -- DEGREES --, therefor.
In Fig. 2E, Sheet 8 of 18, delete "DEGREE ROTATION" and insert -- DEGREE OF ROTATION --, therefor.

IN THE SPECIFICATION:
In Column 10, Line 31, delete "inchs/" and insert -- inches/ --, therefor.
In Column 11, Line 39, delete "chamber 120" and insert -- chamber 20 --, therefor.
In Column 13, Line 15, delete "piston 222 cylinder 220" and insert -- piston 222/cylinder220 --, therefor.

IN THE CLAIMS:
In Column 16, Line 43, in Claim 14, delete "lifter" and insert -- liter, --, therefor.

Signed and Sealed this
Twenty-ninth Day of December, 2015

Michelle K. Lee
*Director of the United States Patent and Trademark Office*